United States Patent
Subramaniam et al.

(10) Patent No.: US 8,080,677 B2
(45) Date of Patent: Dec. 20, 2011

(54) PROCESS FOR SELECTIVE OXIDATION OF OLEFINS TO EPOXIDES

(75) Inventors: Bala Subramaniam, Lawrence, KS (US); Daryle H. Busch, Lawrence, KS (US); Hyun-Jin Lee, Lawrence, KS (US); Madhav Ghanta, Lawrence, KS (US); Tie-Pan Shi, Bartlesville, OK (US)

(73) Assignee: University of Kansas, Lawrence, KS (US)

( * ) Notice: Subject to any disclaimer, the term of this patent is extended or adjusted under 35 U.S.C. 154(b) by 398 days.

(21) Appl. No.: 12/206,335

(22) Filed: Sep. 8, 2008

(65) Prior Publication Data

US 2009/0131693 A1 May 21, 2009

Related U.S. Application Data

(63) Continuation-in-part of application No. 11/586,061, filed on Oct. 25, 2006, now Pat. No. 7,649,101.

(60) Provisional application No. 60/729,941, filed on Oct. 25, 2005.

(51) Int. Cl.
C07D 303/00 (2006.01)

(52) U.S. Cl. ........................ 549/513; 549/512

(58) Field of Classification Search .................. 549/512, 549/513
See application file for complete search history.

(56) References Cited

U.S. PATENT DOCUMENTS

| 5,155,247 A | 10/1992 | Herrmann et al. |
| 5,166,372 A | 11/1992 | Crocco et al. |
| 5,618,958 A | 4/1997 | Tucker et al. |
| 5,723,636 A | 3/1998 | Fenelli et al. |
| 5,939,568 A | 8/1999 | Sharpless et al. |
| 6,271,400 B2 | 8/2001 | Sharpless et al. |
| 7,649,101 B2 * | 1/2010 | Busch et al. .................. 549/531 |

FOREIGN PATENT DOCUMENTS

| EP | 1 346 986 | 9/2003 |
| FR | 2 862 302 | 5/2005 |
| WO | WO 01/77052 A1 | 10/2001 |
| WO | WO 02/085875 A1 | 10/2002 |

OTHER PUBLICATIONS

Lee et al., *A Greener, Pressure Intensified Propylene Epoxidation Process with Facile Product Separation*, Chem. Eng. Sci. 62 7282-7289 (e-publ. Aug. 19, 2007).

(Continued)

*Primary Examiner* — Taylor Victor Oh
(74) *Attorney, Agent, or Firm* — Stinson Morrison Hecker LLP

(57) ABSTRACT

A process for the selective oxidation of olefins to epoxides comprising the step of contacting the olefin (propylene or ethylene) with an oxidant (hydrogen peroxide) in the presence of a Lewis acid oxidation catalyst (MTO), organic base (pyridine or its N-oxide), in a solvent system comprising an organic water-miscible solvent (methanol). The system is pressurized using either the olefin itself or by adding an inert pressurizing gas (nitrogen) to increase the pressure between 230 and 700 psi at a temperature between 0.7 and 1.3 times the critical temperature of the olefin. The resulting increased solubility of the olefin in the organic solvent system increases the selectivity and yield of the desired epoxide (propylene oxide or ethylene oxide).

61 Claims, 12 Drawing Sheets

OTHER PUBLICATIONS

Yin et al., *Homogeneous Catalysis for Selective and Light Olefin Epoxidations*, Am. Chem. Sock. Div. Petr. Chem. 52 246-249 (Aug. 2007).

Rajagopalan et al.; "Homogeneous Catalytic Epoxidation of Organic Substrates in CO 2-Expanded Solvents in the Presence of Water-Soluble Oxidants and Catalysts", Ind. Eng. Chem. Res., vol. 42, No. 25, Dec. 10, 2003, pp. 6505-6510.

European Search Report dated Sep. 23, 2009 for European Patent Application No. 06826630.3; 7pages.

* cited by examiner

US 8,080,677 B2

PROCESS FOR SELECTIVE OXIDATION OF OLEFINS TO EPOXIDES

CROSS-REFERENCE TO RELATED APPLICATIONS

This application is a continuation-in-part application of and claims priority to U.S. patent application Ser. No. 11/586,061 filed on Oct. 25, 2006, which is based on and claims priority to U.S. Provisional Application Ser. No. 60/729,941, filed on Oct. 25, 2005, which are hereby incorporated by reference.

STATEMENT REGARDING FEDERALLY SPONSORED RESEARCH OR DEVELOPMENT

This present invention was supported in part by the National Science Foundation Engineering Research Centers Grant EEC-0310689. The government has certain rights in the present invention.

BACKGROUND OF THE INVENTION

The epoxidation of olefins, such as propylene to propylene oxide ("PO"), on the industrial scale is among the most challenging chemical processes. Propylene oxide is mainly used for the production of propylene glycol and polyester, and is the starting material for polyurethane, unsaturated resins, and other products.

Industrially over 4.5 million tons of propylene oxide is produced each year using either the chlorohydrin or Halcon process. In the chlorohydrin process, propylene reacts with chlorine and water to produce 1-chloro-2-propanol and HCl, which is then treated with base to generate propylene oxide and salt. There are two pounds of salt waste for each pound of propylene oxide produced. The process consumes large amounts of chlorine and lime which are finally converted to useless and environmentally polluting waste.

The Halcon or hydroperoxide process, organic peroxides are produced, and epoxidation is performed in the presence of transition metal catalysts leading to the formation of propylene oxide and co-products. The economic viability of this process depends on the market value of the co-products because 3 to 4 times more co-product is produced than the weight of propylene oxide produced. Direct oxidation of propylene to propylene oxide with oxygen would be highly desirable, but the presence of propylene's highly reactive allylic hydrogens renders this approach quite difficult.

Minimizing waste in the selective oxidation of propylene to propylene oxide has long been an important objective of industrial chemistry. So-called titanium-substituted silicalite ("TS-1") catalysts can catalyze this reaction with reasonable efficiency using aqueous hydrogen peroxide ($H_2O_2$) and gaseous $O_2/H_2$. TS-1 catalysts have high catalytic activity and selectivity. However, the method is problematic because the catalyst is rapidly deactivated and high temperature is required to regenerate the catalyst. U.S. Pat. No. 5,155,247 entitled "Use of Organorhenium compounds for the oxidation of multiple C—C bonds, oxidation processes based thereon and novel organorhenium compounds" to Herrmann et al. employed a methyltrioxorhenium ($CH_3ReO_3$, hereafter identified as "MTO") catalyst to alkene oxidation under low temperature (below 10° C.) conditions, using hydrogen peroxide as the oxidant. This low temperature process produced propylene oxide and propylene glycol ("PG") in the ratio of 1:1. Herrmann focused on anhydrous hydrogen peroxide (preferably in tert-butanol as a solvent) because water was detrimental to hydrolytic epoxide ring opening. In U.S. Pat. No. 5,166,372 entitled "Epoxidation Process," Crocco et al. improved the selectivity for propylene oxide by employing an alkyl aryl secondary alcohol in the reaction mixture. Magnesium sulfate was used to remove water from the system. In Sharpless, U.S. Pat. No. 5,939,568, nitrogenous aromatic heterocycles were employed as "accelerants" in methylene chloride solvent systems. Lastly, in Sharpless, U.S. Pat. No. 6,271,400, anhydrous oxidants (trialkyl silyl peroxides) and water removal agents were used to reduce the water concentration in the reaction mixture.

Ethylene oxide is a widely used industrial organic intermediate with a worldwide demand in 2006 of 18 million tons, and anticipated annual growth rate of 1.7%. Currently ethylene oxide technology involves either air or $O_2$ oxidation of ethylene using a silver-based catalyst. Typically, the ethylene conversion is maintained at a low level to minimize combustion products. The maximum ethylene conversion is in the range of 10-15% with less than 10% being more typical, and the maximum ethylene oxide selectivity is 85-90%, the byproduct being mainly carbon dioxide formed from the combustion of both ethylene and ethylene oxide. It has also been reported that up to 30% of the ethylene converted may undergo combustion to form carbon dioxide and water (EPA-450/4-84-007L). Among industrial chemical technologies, the ethylene oxide process is one of the largest emitters of carbon dioxide as the ethylene oxide byproduct. Since ethylene accounts for 70-80% of the cost of the product, the burning of ethylene and the product result in value destruction, the generation of waste, and an environmental hazard. Hence, the development of robust catalysts that maximize ethylene oxide selectivity continues to be of paramount interest to industry.

Safety is a major concern in conventional ethylene oxide processes due to the potential for formation of explosive ethylene/ethylene oxide/air mixtures in the gas phase under reaction conditions. Ethylene oxide is a highly explosive substance with a lower flammability limit of 3 mol % and an upper flammability extending to pure ethylene oxide, which is susceptible to spontaneous explosive decomposition by a radical mechanism. Thus, it would be desirable to have an alternate ethylene oxide technology that is selective only towards ethylene oxide (thus eliminating the formation of $CO_2$ as a byproduct), while for safety reasons, also avoiding the formation of explosive ethylene oxide/oxygen mixtures in the gas phase. Such a process would significantly reduce the carbon footprint of this large-scale industrial process.

The present invention is directed to an olefin oxide synthesis process, such as for the production of propylene oxide and ethylene oxide, which has a number of advantages over the prior art.

BRIEF SUMMARY OF THE INVENTION

The present invention is directed to a process for the epoxidation of an olefin to the corresponding epoxide using an oxidant, base, catalyst, organic water-miscible solvent, and pressurizing gas. The pressurizing gas is used to drive the olefin substrate into the liquid phase, thereby promoting the yield and rate of the reaction. The present invention preferably occurs at temperatures not exceeding 60° C., and at pressures which increase the concentration of dissolved olefin in the liquid phase. For light olefins, such as ethylene, the olefin by itself may function as the pressurizing gas. Pressure intensification of the kind described herein is achievable up to temperature of the reaction system in the range up to 1.3 times (typically 0.7 to 1.3 times) the absolute critical temperature of the olefin substrate. For ethylene (Tc=9.5° C.), the reaction system is preferably pressurized to a pressure between 230 and 700 psi at a temperature ranging from 0.7 to 1.3 times the critical temperature of the olefin. The much higher Tc of propylene makes pressure intensification readily available well below its critical temperature so that the maximum reaction temperature is determined by considerations other than the critical temperature (e.g., stability of reactants and products).

In a further aspect, the present invention is directed to a reaction mixture or reaction system. The reaction mixture or reaction system comprises an olefin to be epoxidized, an oxidant, a Lewis acid oxidation catalyst, and an organic base in a solvent system comprising an organic water-miscible solvent. A pressurizing gas (e.g., between about 230 to 700 psi) is preferably added so that the olefin is partially dissolved in the organic solvent system in a higher amount than without the pressurizing gas. For light olefins, such as ethylene, the olefin may function as the pressurizing gas so that the system pressure is raised to about 230 to 700 psi.

In one aspect, the olefin is ethylene or propylene, the catalyst is an organorhenium oxide, and the oxidant is hydrogen peroxide in an aqueous solution having about 20 to 80 wt % hydrogen peroxide or is urea hydrogen peroxide. The pressurizing gas is preferably an inert gas, such as nitrogen having a pressure between about 230 and 700 psi, or the reaction system is raised to a pressure of about 230 to 700 psi by feeding additional ethylene or propylene into the system. The organic base is also preferable a nitrogen-containing compound selected such as pyridine and/or its corresponding N-oxide. The water miscible solvent is preferably a lower alcohol, such as methanol. In the case of aqueous hydrogen peroxide oxidants, the water associated with the hydrogen peroxide system will form part of the overall solvent system (along with water produced as a result of the decomposition of the hydrogen peroxide). Preferably, the solvent system comprises methanol and water at a weight ratio between 3:1 to 22:1 for methanol to water.

The temperature of the reaction system is preferably about 0.7 to 1.3 times the critical temperature of the olefin substrate Tc, where Tc is in absolute units (K). Thus, for propylene (Tc=91.8° C. or 365 K, Pc=46 bar or 667 psi), the reaction temperature is preferably 0 to 60° C. (or roughly 0.75 to 0.95 Tc). Similarly, for ethylene (Tc=9.5 C or 282 K, Pc=51 bar or 737 psi), the reaction temperature is preferably 0 to 60° C. (or roughly 0.97 to 1.18 Tc). Most preferably, the reaction occurs at a temperature of about 20 to 30° C.

In another aspect, methods for separating the epoxidized product and recycling the unreacted reactants is provided. For example, in one aspect, the pressure of the system may be decreased to create a vapor phase containing unreacted olefin and a liquid phase comprising the epoxidized olefin, Lewis acid oxidation catalyst, and solvent system. The liquid phase may be fractionated to distill off a first gaseous stream comprising the epoxidized olefin and a second liquid stream comprising the Lewis oxidation catalyst, organic base, and solvent system.

In still another aspect, the water may be separated from the Lewis oxidation catalyst, said organic base, and organic water miscible solvent from the second liquid stream by reverse osmosis. The oxidation catalyst, organic base, and/or organic water miscible solvent may be recycled to the feed stream.

In yet another aspect, the oxidation catalyst, organic base, and/or organic water miscible solvent are separated from the second liquid stream by distillation. Again, the oxidation catalyst, organic base, and/or organic water miscible solvent may be recycled to the feed stream.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1:
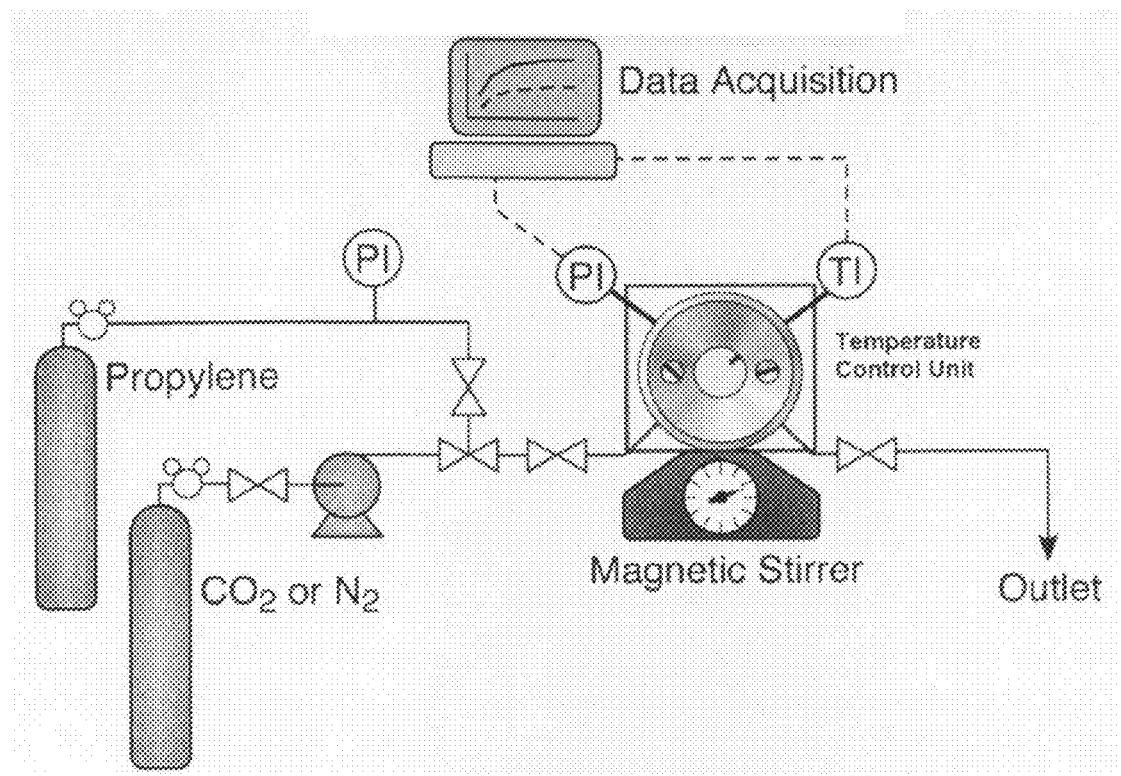
FIG. 1 is a schematic of the reactor used in all examples except Example 2 of the present invention.

The present invention is directed to a process for epoxidizing an olefin comprising the steps of (1) contacting the olefin with an oxidant in the presence of a Lewis acid oxidation catalyst, organic base, in a solvent system comprised an organic water-miscible solvent; and (2) adding a pressurizing gas to increase the pressure, whereby the olefin is further dissolved in said organic solvent system. For light olefins (e.g., ethylene, propylene, butadienes, pentenes, etc.), the olefin itself may function as the pressurizing gas.

The olefins epoxidized in the process of the present invention may be any organic compound having at least one ethylenically unsaturated functional group (i.e., a carbon-carbon double bond) and may be, for example, an aromatic, aliphatic, mixed aromatic-aliphatic (e.g., aralkyl), cyclic, branched or straight chain olefin. Examples are set forth in Sharpless et al., U.S. Pat. Nos. 5,939,568 and 6,271,400, which are incorporated by reference. Preferably, the olefin contains from 2 to 30 carbon atoms (i.e., a $C_2$-$C_{30}$ olefin). More than one carbon-carbon double bond may be present in the olefin, and thus, dienes, trienes, and other polyunsaturated substrates thus may be used. Other examples of suitable substrates include unsaturated fatty acids or fatty acid derivatives such as esters or glycerides and oligomeric or polymeric unsaturated compounds such as polybutadiene. The olefin may optionally contain substituents other than hydrocarbon substituents such as halide, carboxylic acid, ether, hydroxy, thiol, nitro, cyano, ketone, ester, anhydride, amino, and the like.

Exemplary olefins suitable in the process of the present invention include ethylene, propylene, the butenes, butadiene, the pentenes, isoprene, 1-hexene, 3-hexene, 1-heptene, 1-octene, diisobutylene, 1-nonene, 1-tetradecene, pentamyrcene, camphene, 1-undecene, 1-dodecene, 1-tridecene, 1-tetradecene, 1-pentadecene, 1-hexadecene, 1-heptadecene decene, 1-nonadecene, 1-eicosene, the trimers and tetramers of propylene, polybutadiene, polyisoprene, cyclopentene, cyclohexene, cycloheptene, cyclooctene, cyclooctadiene, cyclododecene, cyclododecatriene, dicyclopentadiene, methylenecyclopropane, methylenecyclopentane, methylenecyclohexane, vinylcyclohexane, vinyl cyclohexene, methallyl ketone, allyl chloride, allyl bromide, acrylic acid, methacrylic acid, crotonic acid, vinyl acetic acid, crotyl chloride, methallyl chloride, the dichlorobutenes, allyl alcohol, allyl carbonate, allyl acetate, alkyl acrylates and methacrylates, diallyl maleate, diallyl phthalate, unsaturated triglycerides such as soybean oil, and unsaturated fatty acids, such as oleic acid, linolenic acid, linoleic acid, erucic acid, palmitoleic acid, and ricinoleic acid and their esters (including mono-, di-, and triglyceride esters), and alkenyl aromatic compounds such as styrene, .alpha.-methyl styrene, .beta.-methyl styrene, divinyl benzene, 1,2-dihydronaphthalene, indene, stilbene, cinnamyl alcohol, 2-methyl-1-phenyl-1-propene, 2-methyl-3-phenyl-2-propen-1-ol, cinnamyl acetate, cinnamyl bromide, cinnamyl chloride, 4-stilbenemethanol, ar-methyl styrene, ar-ethyl styrene, ar-tert-butyl styrene, archlorostyrene, 1,1-diphenylethylene, vinyl benzyl chloride, vinyl naphthalene, vinyl benzoic acid, ar-acetoxy styrene, ar-hydroxy styrene (i.e., vinyl phenol), 2- or 3-methyl indene, 2,4,6-trimethylstyrene, 1-phenyl-1-cyclohexene, 1,3-diisopropenyl benzene, vinyl anthracene, vinyl anisole, and the like. Of these, propylene and ethylene are most preferred. The olefin is preferably present in about 2 to 20 mol % of the reaction mixture. It will be appreciated by those skilled in the art that the olefin concentration (i.e., availability) in the liquid phase (i.e., 2 to 20 mol %), where the reaction occurs, is most important, and for low boiling light olefins this is dictated by the operating pressure and temperature. The liquid phase preferably contains at least a stoichiometric amount of the oxidant required to make complete olefin (e.g., propylene or ethylene) conversion to epoxide (e.g., propylene oxide or ethylene oxide) possible.

The oxidant used in the present invention comprises hydrogen peroxide. Hydrogen peroxide is typically commercially available in the form of a solid urea (anhydrous) form or aqueous solution, typically 30 to 50 wt % is commercially available. Thus, as discussed more fully below, that water may form part of the overall solvent system of the reaction mixture, along with a suitable organic water-miscible solvent. The oxidant is preferably present in the reaction mixture at a concentration of about 4 to 16 mol %. As discussed above, the oxidant is present in a stoichiometric amount for complete epoxidation of the olefin (e.g., propylene to propylene oxide) to occur.

The base used in the present invention preferably comprises a saturated or unsaturated amine or corresponding N-oxide. Examples are set forth in Sharpless, U.S. Pat. Nos. 5,939,568 and 6,271,400, which are incorporated by reference. Suitable organic nitrogen bases are, for example, methylamine, diethylamine, propylamine, octylamine, trimethylamine, dimethyldodecylamine, cyclohexylamine, dicyclohexylamine, aminoethanol, diethanolamine, triethanolamine, N,N-dributylethanolamine, ethylenediamine, hexamethylenediamine, morpholine, piperidine, pyridine, substituted pyridines, 2,2'-bipyridine and 2,2',2''-tripyridine and their substituted derivatives, imidazole and triazines, and corresponding N-oxides. Of these, pyridine and pyridine N-oxide are most preferred. The amount of base may be determined by the catalyst concentration, and the molar amount of base should be at least the molar equivalent of the catalyst. Typically, the amount of base is about 0.1 to 0.56 mol % with 0.2% being preferred.

The catalyst used in the present invention is preferably a Lewis acid oxidation catalyst, such as organorhenium oxide catalysts (e.g., methyltrioxorhenium), or other high valent rhenium-containing compound. Other suitable but less preferred catalysts include those based on tungsten (e.g., tungstates), molybdenum (e.g., molybdates), and titanium(IV) compounds and vanadium(IV) or vanadium(V) compounds. Such compounds are known to those skilled in the art, and examples are set forth in U.S. Pat. Nos. 5,166,372; 5,155,247; 5,939,568; and 6,271,400, which are incorporated by reference. Typically, about 0.05 to 0.08 mole % of MTO and other catalysts is used. The preferred molar olefin to catalyst ratio is between about 40:1 and 400:1.

The organic water-miscible solvent used in the epoxidation process of the present invention is preferably a lower alcohol ($C_1$-$C_4$), e.g., methanol, ethanol, propanol, isopropanol, tert-butanol, and the like. Other exemplary solvents are those set forth in U.S. Pat. Nos. 5,939,568 and 6,271,400, with tetrahydrofuran, acetonitrile, and aromatic hydrocarbons such as toluene and xylene being preferred. Of these, methanol is especially preferred. In one aspect, the methanol:water weight ratio ranges from 3:1 to 22:1 methanol over water, with weight ratios of 13:1 to 22:1 being preferred. It will be appreciated that water may be present in the initial reaction mixture (e.g., from aqueous hydrogen peroxide) and will also be produced by use of the hydrogen peroxide during the reaction itself.

The pressurizing gas used in the present invention is preferably an inert gas (such as nitrogen, argon, neon, helium, and the like). The pressure ranges between about 100 and 1000 psi, although pressures between about 230 and 700 psi are most preferred. For light olefins, such as ethylene, the olefin itself may be sufficient to pressurize the system, and in such cases, the inert gas is not required (although amounts of non-olefin pressurizing gas may be used to further drive the light olefin into the liquid phase).

For the Examples 1 to 10, a cylindrical view-cell reactor as generally set forth in FIG. 1 was constructed. The reactor was made of titanium and has two end caps fitted with two sapphire windows, a gas inlet valve, and a gas outlet valve as shown in FIG. 1. The reactor was interfaced with a pressure transducer, a thermocouple, and a pressure relief valve. The pressure and temperature were computer-monitored during the reaction. The reactor was heated with a band heater for the 1, 3, 6, and 12-hour reaction periods in fixed-time batch experiments.

As discussed in Examples 1-11, introduction of the pressurizing inert gas intensified the reaction, producing high yields of the desired epoxide product. The inert gas preferentially partitions the olefin (e.g., propylene) into the liquid phase. The yield is greater than 50% propylene oxide, even more preferably greater than 75%, still even more preferably greater than 90%, and most preferably greater than 95% and even greater than 99%.

Further, Example 12 shows that the critical temperature of ethylene (Tc=9.5° C.) can be exploited to significantly increase its solubility in a liquid reaction phase by facile compression beyond the critical pressure of ethylene (Pc=50.8 bar or 737 psi). Because hydrogen peroxide is stable at typical reaction temperatures (preferably 60° C. or less and most preferably 40° C. or less), potentially explosive $EO/O_2$ mixtures are avoided in the gas phase.

Example 1

Oxidation of Propylene with Carbon Dioxide as the Pressurizing Gas

In this example, the effect of adding dense carbon dioxide to the reaction mixture was investigated in various organic solvent systems and bases. More specifically, in this example, the reactor was charged with 0.0120 g (0.049 mmol) MTO, 0.610 ml aqueous hydrogen peroxide (50 wt % in water, density 1.18 g/ml) (10.58 mmol) in either 4.14 ml methanol or 4.0 ml acetonitrile as the organic solvent, with 0.40 ml (4.965 mmol) pyridine or 0.049 g (0.51 mmol) pyridine N-oxide as the base.

After introduction of 100 mg (2.376 mmol) propylene, carbon dioxide (2.37 ml, about 700 psi at 25° C.) was then added to the reactor by bubbling through the liquid at a predetermined pressure (700 psi) selected to produce a single liquid phase in the reactor. In addition to the carbon dioxide pressure, the reaction mixture compositions were chosen to produce a single liquid phase in the reactor. The reaction was monitored for about three hours at about 40° C.

At the conclusion of the reaction period, the propylene oxide was separated by a simple distillation method and the amount of the propylene oxide was determined by gas chromatography ("GC") or GC combined with mass spectrometry ("GC/MS").

As shown in Table 1 below, the highest yield of propylene oxide was produced with a methanol/water as the solvent system and pyridine N-oxide as the base. It should be noted that the water that forms part of the solvent system comprises both the water in the aqueous hydrogen peroxide reactant solution and water formed as part of the hydrogen peroxide use during the reaction. The high solubility of propylene in methanol produces the higher yield of propylene oxide than that obtained with acetonitrile. The selectivity favors propylene oxide as the product by over 95% in all cases using methanol as the organic solvent. Trace amounts of propylene glycol in the $CO_2$/acetonitrile example or 1-methoxy-2-propanol in the $CO_2$/methanol example were produced during the reactions (data not shown).

TABLE 1

Propylene oxidation with $CO_2$ Expanded Liquid Solvent System

| Ex. | Base | Organic solvent | Yield of PO (%) | Selectivity (%) |
|---|---|---|---|---|
| 1 | None | Acetonitrile | 14.65 | N/A |
| 2 | Pyridine | Acetonitrile | 18.20 | N/A |
| 3 | Pyridine | Methanol | 60.25 | 98 |
| 4 | Pyridine N-oxide | Methanol | 78.73 | 96 |

Example 2

Propylene Solubility in Methanol/Water Solvent System at Different Pressures

Figure 2:
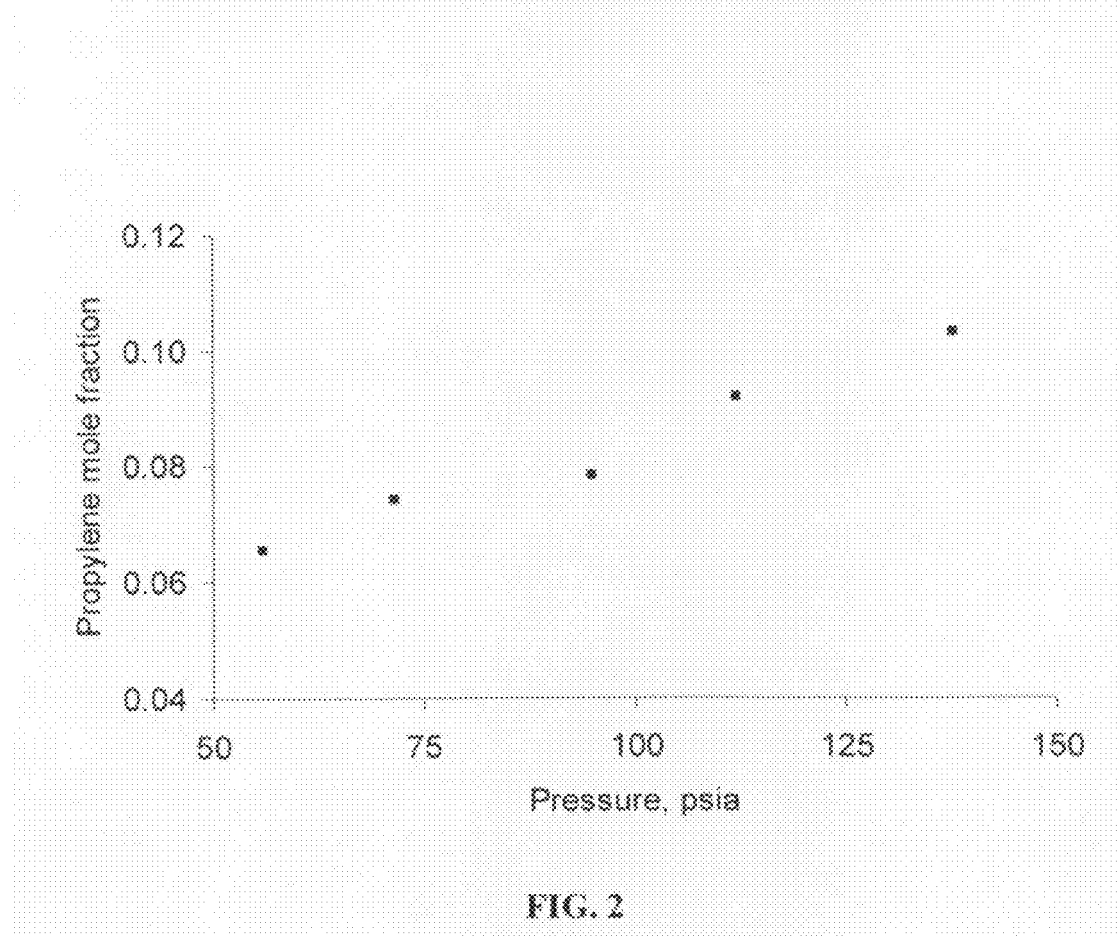
FIG. 2 shows propylene solubility in a methanol/water (6:1 wt ratio) medium as a function of propylene pressure.

In this example, the propylene solubility in the methanol/water solvent system was investigated at different pressures. A methanol/water weight ratio of 6:1 was used in this example. In this example, propylene was fed to the reactor to reach various system pressures by adjusting the amount of propylene. The solubility of propylene in the liquid phase was measured by GC equipped with both capillary and packed columns. At 40° C., the mole fraction of propylene in the liquid phase is shown in FIG. 2 and increases, as expected, with applied propylene pressure.

Example 3

Effects of Different Bases on Propylene Oxide Yield and Selectivity

In this example, several different organic nitrogen-containing bases were investigated to determine effects on yield and selectivity. More specifically, in this example, the reactor was charged with 0.0120 g (0.049 mmol) MTO, 0.610 ml aqueous hydrogen peroxide (50 wt % in $H_2O$) in 4.14 ml methanol as the organic solvent and a base as set forth in Table 2 below. Carbon dioxide (700 psi) was added as in Example 1. The bases pyridine, pyridine N-oxide, 4,4'-dipyridyl, 2,2'-dipyridyl N,N'-dioxide, 2,2'-6,2"-terpyridine, 2,4,6-tri(4-pyridyl)-1,3,5-triazine, and diphenylamine were studied in search of the optimal co-factor for propylene oxidation. As shown in the table below, pyridine-N-oxide produced the highest yield in methanol at 40° C. in the presence of 700 psi carbon dioxide.

TABLE 2

Base Effect of Propylene Oxidation with MTO for 3-Hour Reaction in Carbon-Dioxide Expanded Liquid

| Ex. | Base | Amount | Yield of PO (%) | Temp (° C.) | Reaction time (hour) |
|---|---|---|---|---|---|
| 3 | Pyridine | 0.40 ml (4.96 mmol) | 60.25 | 40 | 3 |
| 4 | Pyridine N-oxide | 48.8 mg (0.512 mmol) | 72.73 | 40 | 3 |
| 5 | Pyridine N-oxide | 9.76 mg (0.102 mmol) | 51.10 | 40 | 9 |
| 6 | Diphenylamine | 23.1 mg (0.137 mmol) | 31.48 | 40 | 3 |
| 7 | 2,2'-Dipyridyl N,N'-dioxide | 10.8 mg (0.057 mmol) | 50.34 | 30 | 3 |
| 8 | No base | | 51.08 | 40 | 3 |

Example 4

Effect of Nitrogen as Pressurizing Gas on Yield and Selectivity

In this example, the effect of using nitrogen as the pressurizing gas was investigated. More specifically, in this example, the reactor was charged with 0.0120 g (0.049 mmol) MTO, 0.27 ml aqueous hydrogen peroxide (50 wt % in $H_2O$) (4.685 mmol) in 4.14 ml methanol as the organic solvent, and 0.049 g (0.512 mmol) pyridine N-oxide as the base.

After the propylene (100 mg) was charged into the reactor, pressurized nitrogen was added to give a pressure equivalent to that in previous reactions using a carbon dioxide pressurized system (700 psi). Various nitrogen pressures were examined as shown in the table below. For each experiment, the reaction time was about three hours (error ±5%), and the temperature was maintained at about 40° C.

TABLE 3

Nitrogen and pressure effect for propylene oxidation.

| Ex. | Pressurizing Gas | Pressure | Yield of PO (%) | Selectivity | By-Products (wt %) |
|---|---|---|---|---|---|
| 4 | $CO_2$ | ~700 psi | 72.73 | >95 | 1.85% 1M2P 0.59 PG |
| 9 | $N_2$ | ~700 psi | >99 | >95 | 2.3% 1M2P |
| 10 | $N_2$ | ~230 psi | >98 | >95 | 1.02% 1M2P |
| 11 | None | ~35 psi | 82.58 | >95 | |

* PG = propylene glycol;
1M2P = 1-methyl-2-propanol

Example 5

Effect of Nitrogen as Pressurizing Gas on Substrate Solubility

The reactor pressure with propylene (100 mg) and water was about 90 psi (data not shown). As shown in the Table 3 above, when methanol (instead of water alone) was used as a co-solvent, the reactor pressure with methanol is reduced by about 55 psi to only 35 psi because of the solubility of propylene in the methanol/water solvent system.

Figure 3A:
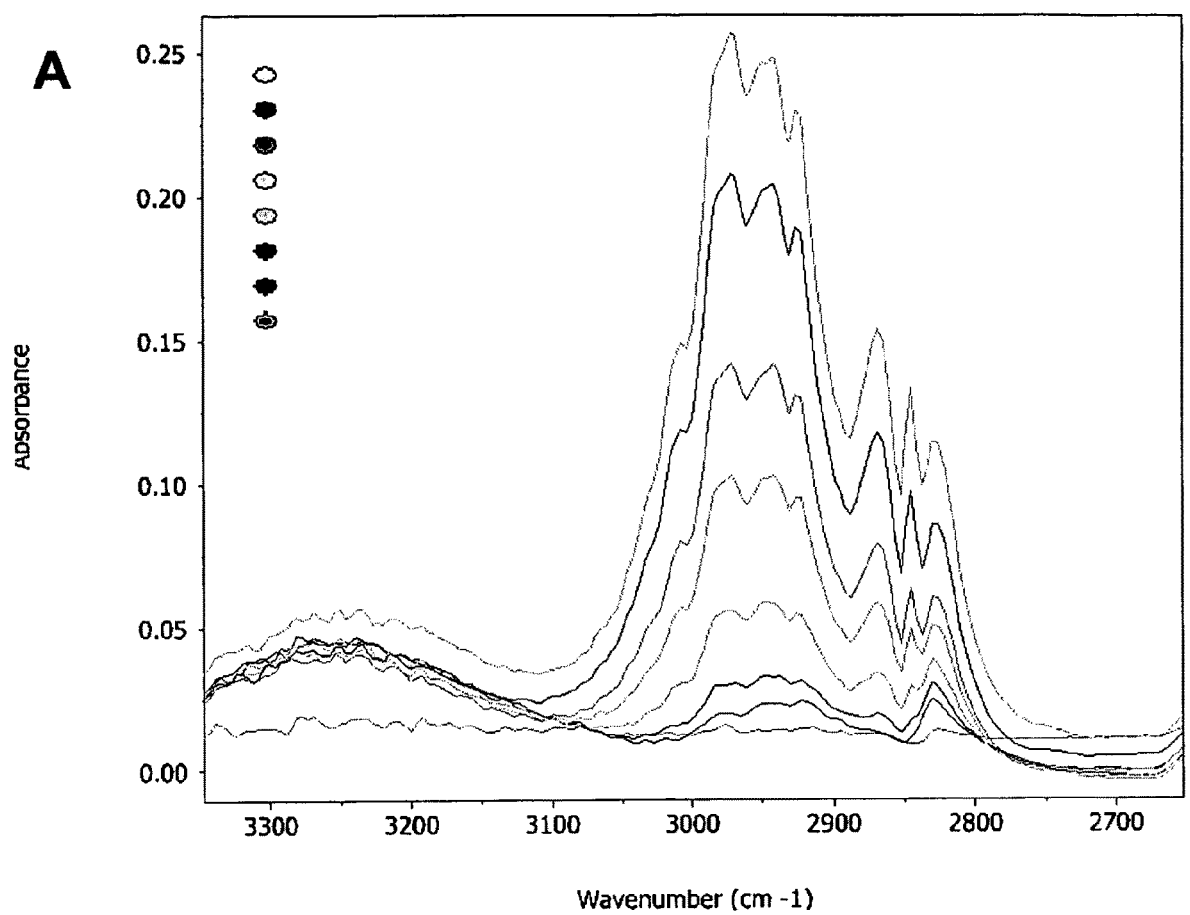
FIG. 3 shows the alkene C—H stretching vibration band around 3000 $cm^{-1}$ at various pressures. Spectral changes due to pressure increases indicate the increased solubility of propylene.
Figure 3B:
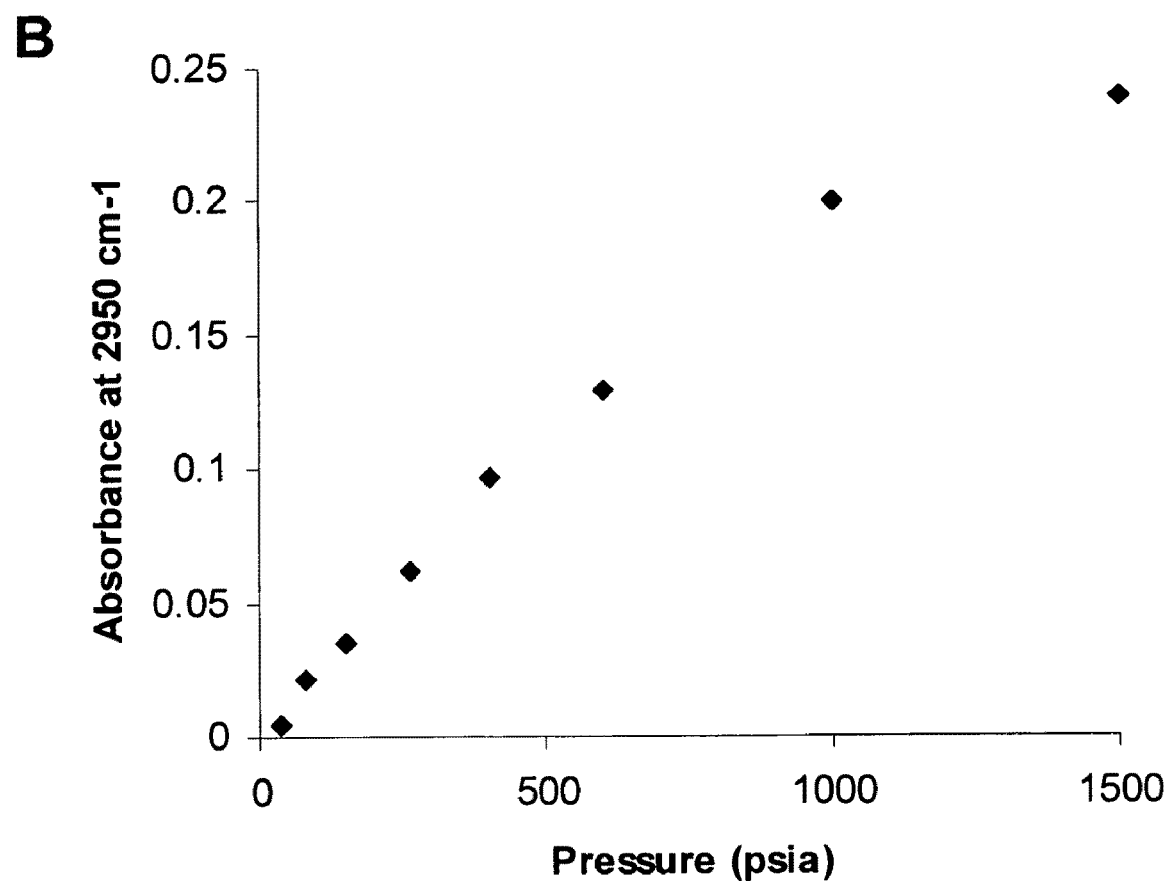

The foregoing examples suggest that increased conversion at higher nitrogen pressures should be attributed in part to enhanced, propylene solubility in methanol. Indeed, as shown in FIG. 3, in situ ReactIR studies in a stirred vessel show that the concentration of propylene in the liquid methanol/water phase at progressively increasing nitrogen pressures.

To test this, experimental measurements reveal increased propylene solubility, albeit modest, in the liquid phase under increasing nitrogen pressure. The experiments were performed with a 6:1 weight methanol/water liquid phase mixture. The temperature was held at 40° C. and the propylene partial pressure in the gas phase was maintained constant at nearly 44 psi. The total pressure of the system was then increased by adding various partial pressures of nitrogen and then measuring the equilibrium propylene solubility in the liquid phase. The results are as shown in Table 4:

TABLE 4

Propylene solubility in Methanol/Water (6:1 weight ratio) medium at 40° C.

| Pressure (psi) | Propylene solubility in liquid phase (mole fraction) |
|---|---|
| 44 psi propylene | 0.0623 |
| 44 psi propylene + 105 psi $N_2$ | 0.0680 |
| 44 psi propylene + 206 psi $N_2$ | 0.0715 |

The enhanced solubility of propylene under pressurized nitrogen increases the yield of propylene oxide over that found for the reaction in the carbon dioxide pressurized system or with no added gas.

Example 6

Effect of Solvent on Product Yield

Figure 4:
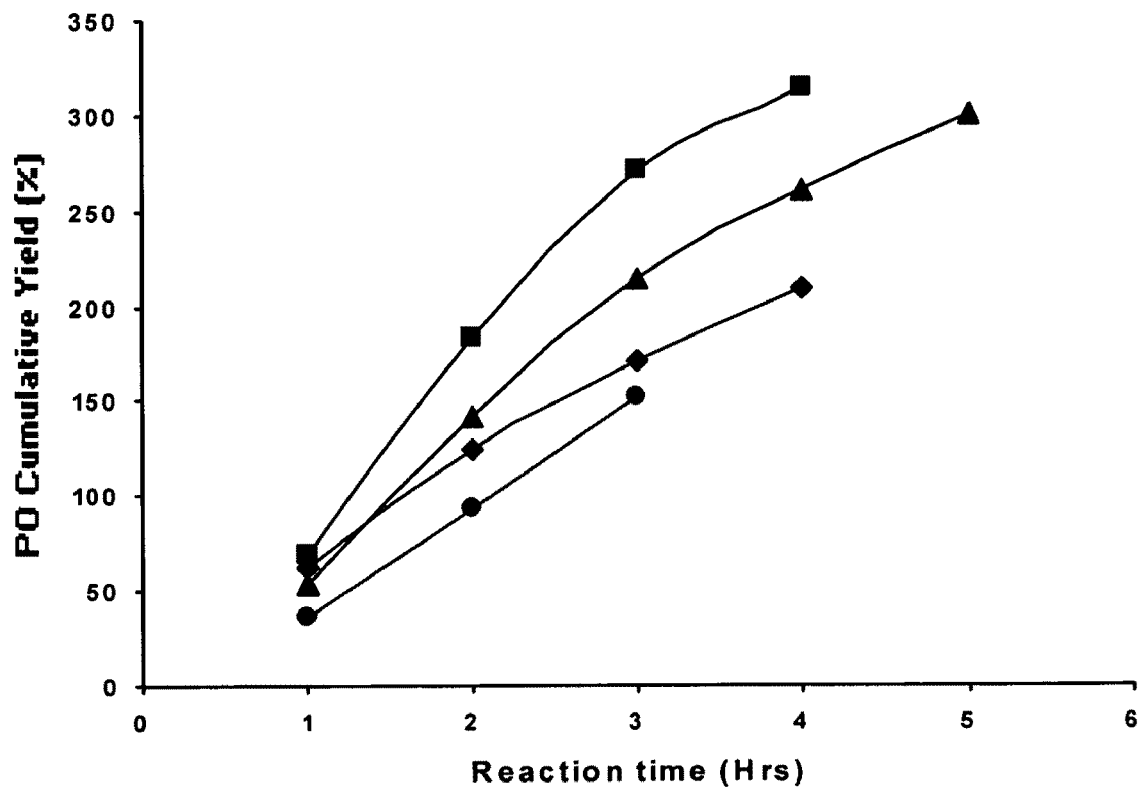
FIG. 4 shows the effect of solvent on propylene oxidation (■: $CH_3OH$; ▲: tert-BuOH; ♦: $CH_3CN$; ●: isopropanol).

In this example, the effect of various organic solvents on product yield was investigated. Several different alcohols, including methanol, isopropanol and tert-butanol, and acetonitrile ($CH_3CN$), were used to test catalyst stability. The reactor was charged with MTO (0.0120 g, 0.049 mmol), pyridine-N-oxide (0.0144 g, 0.151 mmol) and 0.27 ml aqueous hydrogen peroxide (50 wt % in $H_2O$) (4.684 mmol) in 4.14 ml of one of the organic solvents. Propylene (100 mg, 2.376 mmol) was charged into the reactor which was then pressurized with $N_2$ at 30° C. at 250 psi. In order to repeat the reaction, fresh propylene and $H_2O_2$ were added to the reactor after the first one-hour reaction. Products were analyzed by GC at the end of each one-hour cycle. The order of catalyst stability was then judged by the cumulative product yield: isopropanol<acetonitrile<tert-butanol<methanol, as shown in FIG. 4.

Example 7

Effect of Temperature on Product Yield

In this example, the effect of reaction temperature on product yield was investigated. More specifically, propylene oxidation with MTO was carried out at 20, 30, and 40° C. The reactor was charged with MTO (0.0120 g, 0.049 mmol), pyridine N-oxide (0.0144 g, 0.151 mmol) and 0.27 ml aqueous hydrogen peroxide (50 wt % in $H_2O$) (4.684 mmol) in 4.14 ml of methanol as the organic solvent. The propylene (100 mg, 2.376 mmol) was charged into the reactor which was then pressurized with $N_2$ at 250 psi. Fresh propylene and $H_2O_2$ was added after each 1-hour reaction and products were monitored by GC.

Figure 5:
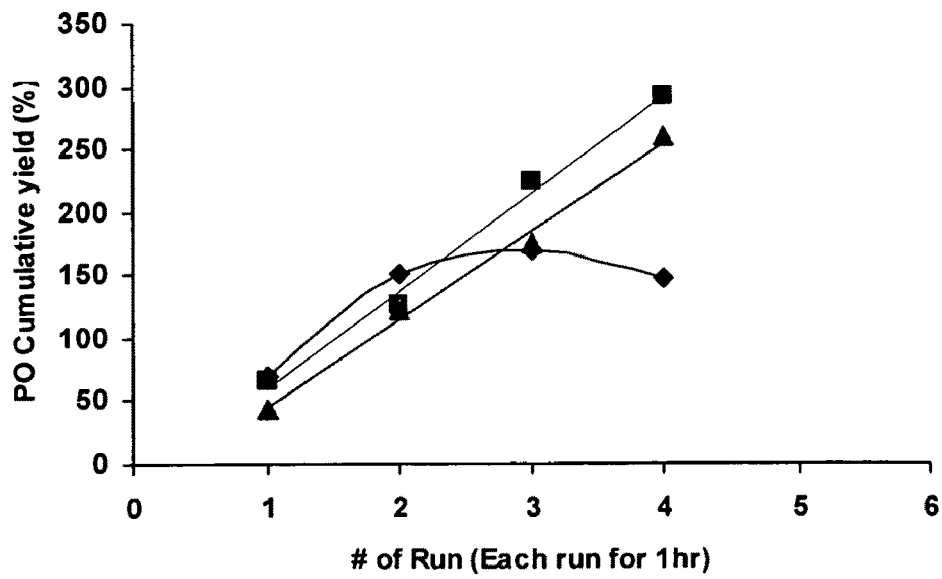
FIG. 5 shows the effect of temperature on propylene oxidation (■: 30° C.-pyNO: color disappeared after 12 hrs; ▲: 20° C.-pyNO; ♦: 40° C.-pyNO: color disappeared after third run).

The results are shown in FIG. 5. On the time scale of these reactions, the optimal reaction temperature is between about 20 and 30° C. In the course of these studies, it became apparent that the color of the solution is a strong indicator of the condition of the catalyst. In accord with the literature (Abu-Omar et al., *Deactivation of Methylrhenium Trioxide-Peroxide Catalysts by Diverse and Competing Pathways*, J. Am. Chem. Soc., 4966-4974 (1996)), the solution maintains a yellow color so long as the diperoxo derivative of MTO is the dominant species in solution. As long as this color is stable, the catalyst performance is stable. Significantly, the color of the solution studied at 20° C. remained a strong yellow even though the cumulative yield of product was uniformly a little lower than that for the system operating at 30° C. It is important to note that the latter solution became colorless after approximately 12 hours. These results indicate that the catalyst, while exhibiting higher propylene oxide formation activity at higher temperatures, also deactivates more rapidly at those temperatures. Decreasing the temperature had a clear beneficial effect on the stability of the MTO catalyst as revealed by the cumulative yield of propylene oxide.

Example 8

Effect of Peroxide Source on Product Yield

By the very nature of the hydrogen peroxide source, the 50% aqueous solution, all of the studies described above were conducted in a partial aqueous media. In order to provide an evaluation of the effect of the water component of the solvent system on the process, solid urea hydrogen peroxide was used as the hydrogen peroxide source during the reaction. The reactor was charged with MTO (0.0120 g, 0.049 mmol), pyridine N-oxide (0.0144 g, 0.151 mmol) and solid urea hydrogen peroxide (4.684 mmol) or 0.27 ml aqueous hydrogen peroxide (50 wt % water) (4.684 mmol) in 4.14 ml of methanol or tert-butanol. The propylene (100 mg, 2.376 mmol) was charged into the reactor which was then pressurized with $N_2$ (about 250 psi) and heated at 30° C.

Figure 6:
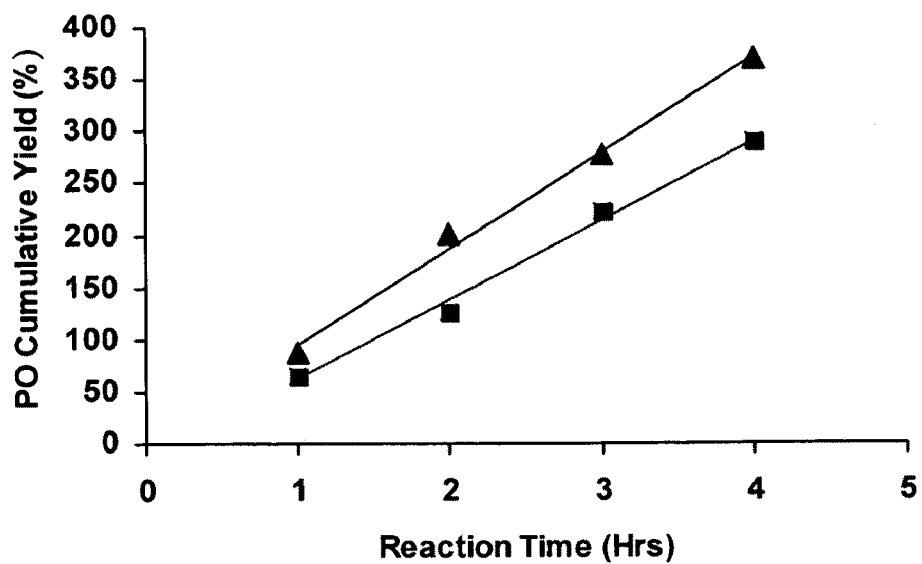
FIG. 6 shows aqueous vs. dry reaction conditions (■: with $H_2O_2$ in 50 wt % $H_2O$; ▲: with urea hydrogen peroxide).

In most of the experiments described herein, the system contained a significant amount of water due to use of 50 wt % hydrogen peroxide in water. The methanol/water ratio did not significantly affect the yield (data not shown), but the yield of PO was substantially increased in the reactions using the dry source of hydrogen peroxide (urea hydrogen peroxide) in methanol, as shown in FIG. 6.

Figure 7:
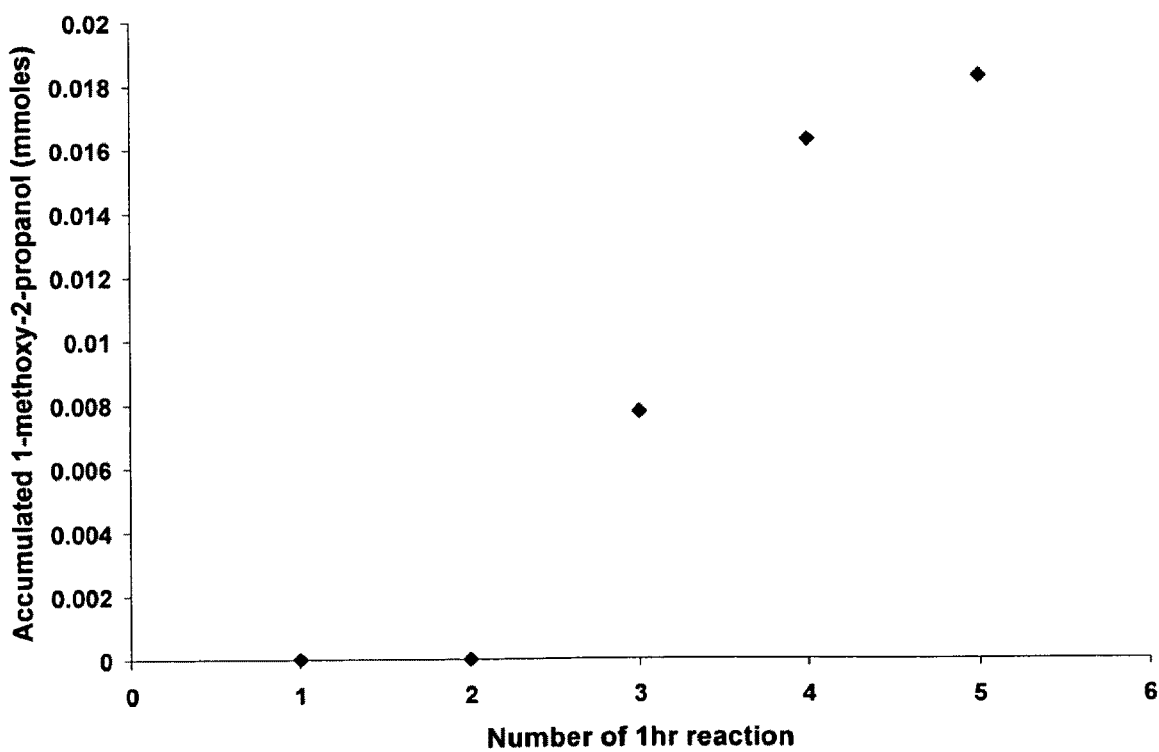
FIG. 7 shows the amount of 1-methoxy-2-propanol byproduct with decreasing methanol/water ratios in continuous reaction data at one-hour reaction period increments with new propylene and oxidant feed.

The amount of 1-methoxy-2-propanol byproduct was affected by the methanol/water ratio. FIG. 7 shows continuous reaction data for five continuous one-hour reaction periods. Reactants were placed in the reactor as in previous examples, and the reaction was allowed to proceed for one-hour periods at 30° C. The products were then analyzed by GC. Fresh propylene and 50 wt % hydrogen peroxide were added to the same reactor, and the reaction was continued for another one-hour reaction. Water accumulates during each reaction period due to the additional water formation from hydrogen peroxide decomposition. FIG. 7 clearly shows increasing concentrations of the unwanted by product 1-methoxy-2-propanol with increasing amounts of water in the solvent system. Thus, the selectivity of propylene oxide production decreased slightly for longer reaction times.

Example 9

Other Olefinic Substrates

In this example, the MTO system was applied to the oxidation of ethylene as the olefin. The reactor was charged with MTO (0.0204 g, 0.082 mmol), pyridine N-oxide (0.02 g, 0.210 mmol) and 0.27 ml aqueous hydrogen peroxide (50 wt % in $H_2O$) (4.684 mmol) in 4.0 ml of methanol as the organic solvent. The ethylene (100 mg, 2.376 mmol) was charged into the reactor which was then pressurized with about 300 psi nitrogen and the reactor was heated at 30° C. After a three-hour batch reaction, ethylene oxide was found as the product with no sign of byproducts such as ethylene glycol.

Example 10

Other Catalyst Systems

Earlier studies found that tungstate catalysts obtained excellent conversion and selectivity for alkene epoxidation. See Sato et al., *A "Green" Route to Adipic Acid: Direct Oxidation of Cyclohexenes with 30 Percent Hydrogen Peroxide*, J. Org. Chem. 61 8310-8311 (1996); Maheswari et al., *A $Na_2WO_4/H_2WO_4$-Based Highly Efficient Biphasic Catalyst towards Alkene Epoxidation, using Dihydrogen Peroxide as Oxidant*, Adv. Synth. Catal. 347 1759-1764 (2005). Strong Lewis acid catalysis is expected since W(VI) is also a high oxidation state. The inorganic tungstate anion is also very stable in the presence of oxidizing agents and at high reaction temperatures. It should also be easily recovered and recycled post reaction. $Na_2WO_4.2H_2O$ and $H_2WO_4$ were applied for propylene oxidation under various conditions as shown Table 6.

TABLE 6

Chemical compositions for studies on tungstate catalysts

| | |
|---|---|
| Propylene | 0.1 g (4.76 mmoles) |
| Organic solvents | $CH_3OH$, $CH_3CN$ (4.0 ml) |
| Catalysts | 0.026 g $Na_2WO_4 \cdot 2H_2O$ (0.078 mmol) |
| | 0.022 g $H_2WO_4$ (0.087 mmol) |
| Phase transfer reagent | Aliquat 336 |
| | 0.5 ml |
| Temperature | 30-70° C. |
| $N_2$ Pressure | 300-800 psi |
| Oxygen source | 1 ml of $H_2O_2$ (50 wt. % in $H_2O$) |

Dissolving tungstic acid in organic solvents presented challenges and may be responsible for the slow reactions indicated by the data in Table 6. The catalysts solubility issue was resolved by using $NH_4OH$ to dissolve the acid, followed by the addition of a strong mineral acid to provide the low pH desired for the solutions.

The reactor was charged with 0.0522 g $Na_2WO_4.2H_2O$ (0.158 mmol), $H_2WO_4$ (0.052 mg, 0.207 mmol) or mixture of 0.026 g $Na_2WO_4.2H_2O$ (0.078 mmol)/0.022 g $H_2WO_4$ (0.087 mmol), 0.0602 mg of chloroacetic acid $ClCH_2COOH$ and 1.0 ml of aqueous hydrogen peroxide (50 wt % in $H_2O$) in 4 ml of methanol as shown in Table 6. Propylene (100 mg, 2.376 mmole) was charged into the reactor which was then pressurized with about 300 psi nitrogen and heated at 40-90° C. The peroxide was rapidly decomposed above 60° C. The catalyst dissolved completely in Experiment 1 which displayed a clear yellow color. The catalyst mixture was only partially dissolved in the $CH_3OH/ClCH_2COOH$ medium in Experiments 3-5. The mixture of catalysts was dissolved in $CH_3OH$ with $NH_4OH$ to improve solubility and a limited amount of $H_2SO_4$ was added in the systems 4 and 5 to return to acidic conditions.

TABLE 7

Propylene oxidation conditions with $Na_2WO_4 \cdot 2H_2O/H_2WO$

| Ex | Catalysts | Additive | Temperature | Products | PO yield |
|---|---|---|---|---|---|
| 1 | $Na_2WO_4 \cdot 2H_2O$ | | 40° C./300 psi $N_2$ | PO | 2%/ 4 hr |
| 2 | $H_2WO_4$ | | 40° C./300 psi $N_2$ | PO + PG | 5.7%/ 4 hr |
| 3 | $Na_2WO_4 \cdot 2H_2O/$ $H_2WO$ | | 40° C./300 psi $N_2$ | PO + PG | 1.5%/ 12 hr |
| 4 | $Na_2WO_4 \cdot 2H_2O/$ $H_2WO$ | $NH_4OH/$ $H_2SO_4$ | 40° C./300 psi $N_2$ | PO + PG | 1.0%/ 12 hr |
| 5 | $Na_2WO_4 \cdot 2H_2O/$ $H_2WO$ | Aliquat 336 | 40° C./300 psi $N_2$ | PO + PG | |

This example thus shows that the epoxidation can occur with very different catalysts, and at very mild conditions. It will be appreciated that those skilled in the art will be able to optimize conditions to further improve the performance of the catalysts discussed herein.

Example 11

Catalyst, Base, and Co-Solvent Recycle

Figure 8:
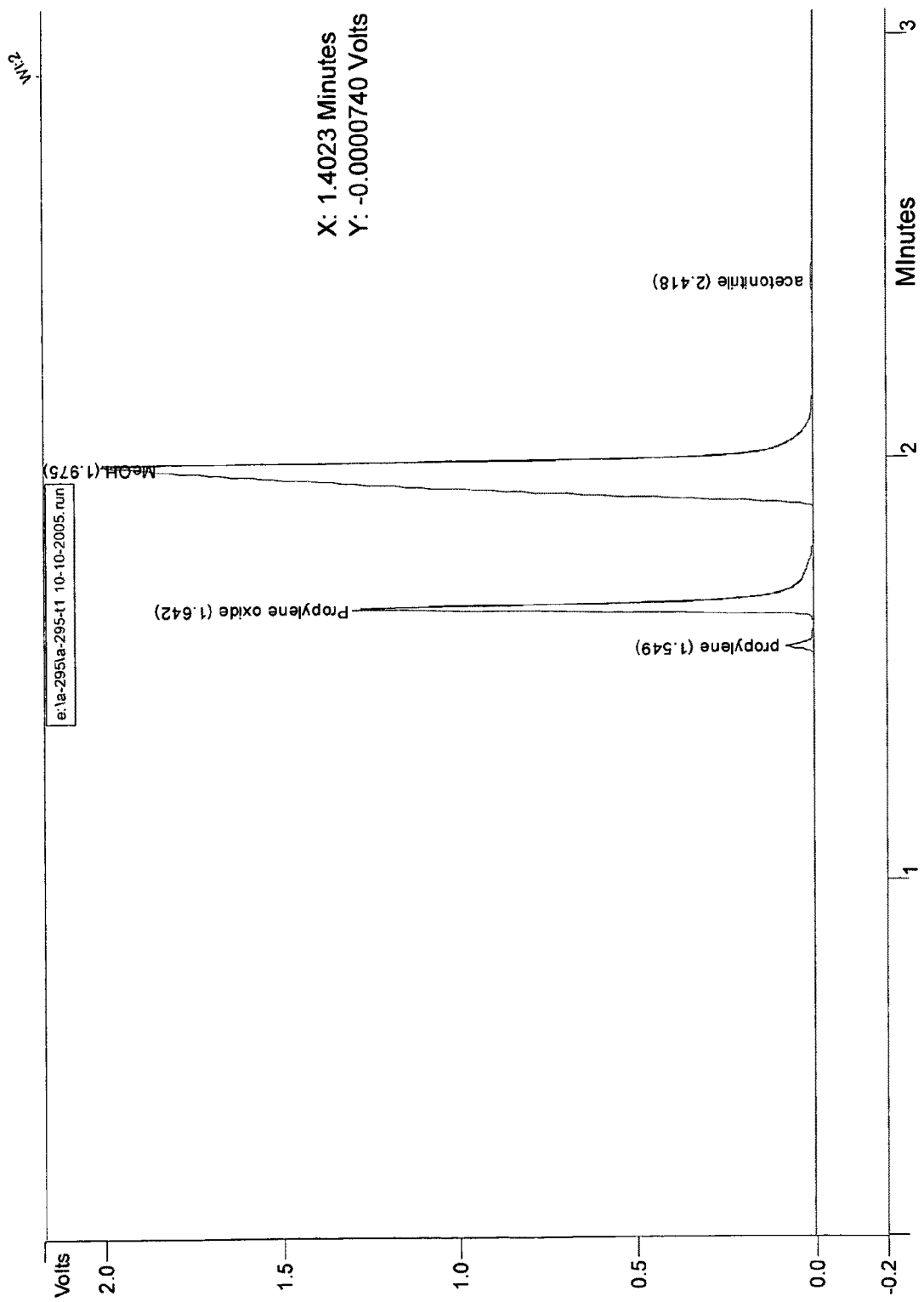
FIG. 8 shows the gas chromatograph results of the separated propylene oxide from Example 11 by simple distillation.

In this example, two methods were applied to evaluate the MTO catalyst recycle. First, a simple distillation was performed at 50° C. after the three-hour reaction as follows. The reactor was charged with MTO (0.0240 g, 0.098 mmol), pyridine-N-oxide (0.3 g, 0.315 mmol), and 1 ml aqueous hydrogen peroxide (50 wt % in $H_2O$) (17.35 mmol) and then charged with 0.3 ml of propylene (7.13 mmol) in a 4.14 ml methanol solvent system and 250 psi nitrogen. The reactor was depressurized to ambient pressure followed by heating of the reaction mixture. At about 40 to 50° C., the propylene oxide boils off leaving the remaining liquid reaction mixture containing mostly water, methanol and dissolved catalyst. The vapor phase propylene oxide is condensed and collected in a dry ice acetone trap. The GC chromatogram after a single stage distillation step shows the efficient separation of propylene oxide from the reactor (FIG. 8). The separated products contain some methanol but multiple stage distillation will improve separation. Secondly, all liquid chemical reagents and the recovered catalyst were dried. The recovered catalyst was reused in the subsequent reaction.

Figure 9:
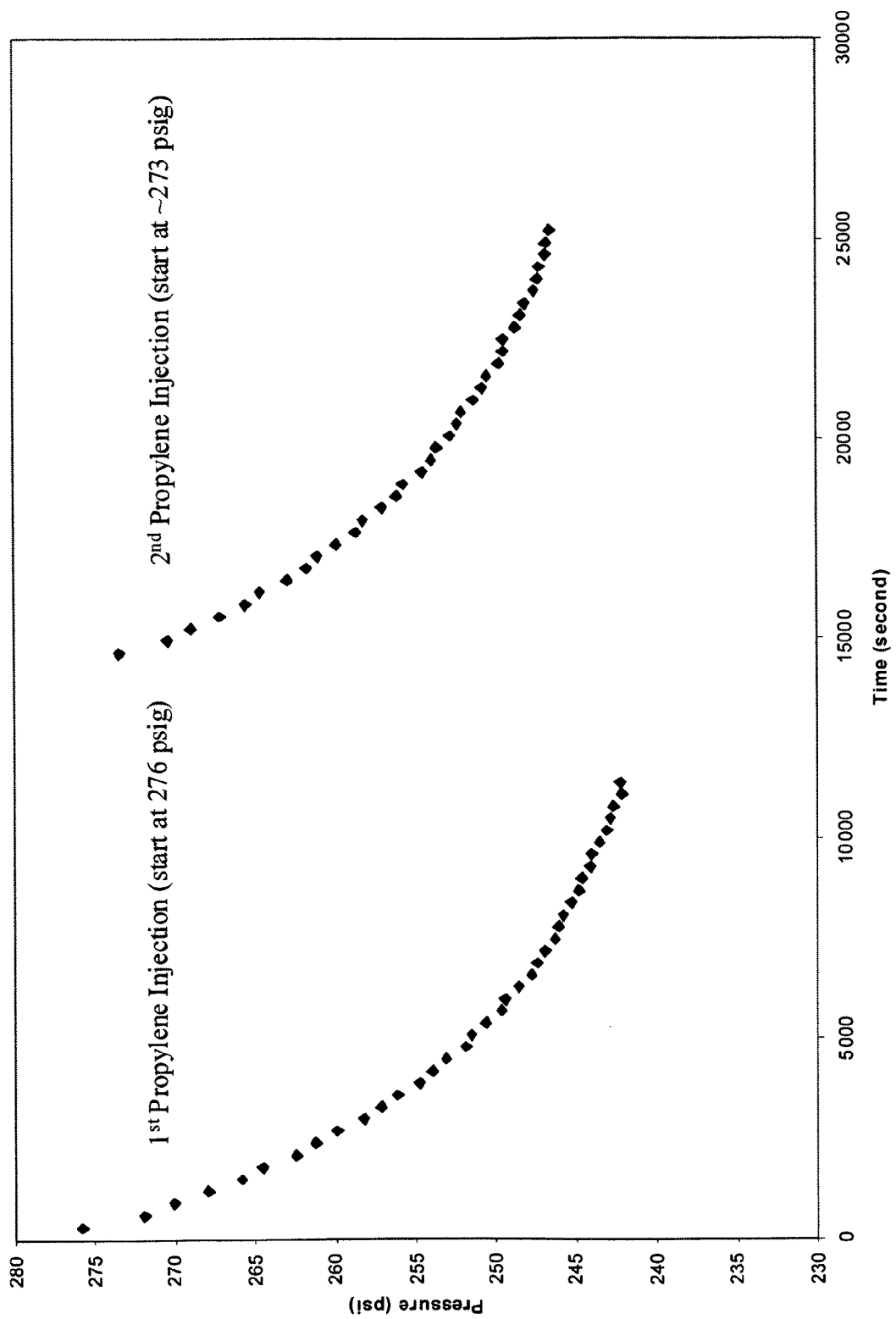
FIG. 9 shows the pressure change between two consecutive reaction cycles. Fresh propylene was charged after the first three-hour reaction.

The stability of the catalyst was examined by multi-cycle reactions. The first reaction was carried out for three hours at 40° C. and products were separated by the simple distillation method and the same amount of fresh propylene was charged in a second reaction cycle. The second reaction was carried out under the same conditions as the first reaction but no hydrogen peroxide and methanol was added. The observed decrease in reactor pressure for the two sequential reactions is almost identical, as shown in FIG. 9. The only gaseous substance affecting the pressure change is believed to be the propylene and, on this basis, the consumption of propylene was judged to be almost the same during the two sequential reactions.

Figure 10:
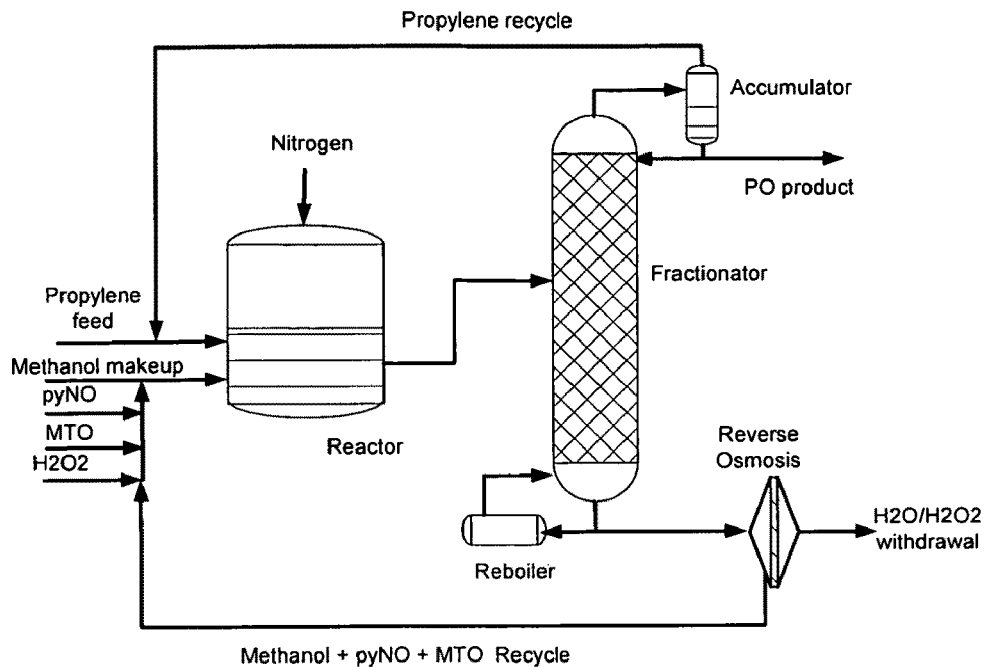
FIG. 10 is a schematic diagram of a propylene oxide process using reverse osmosis water removal system.
Figure 11:
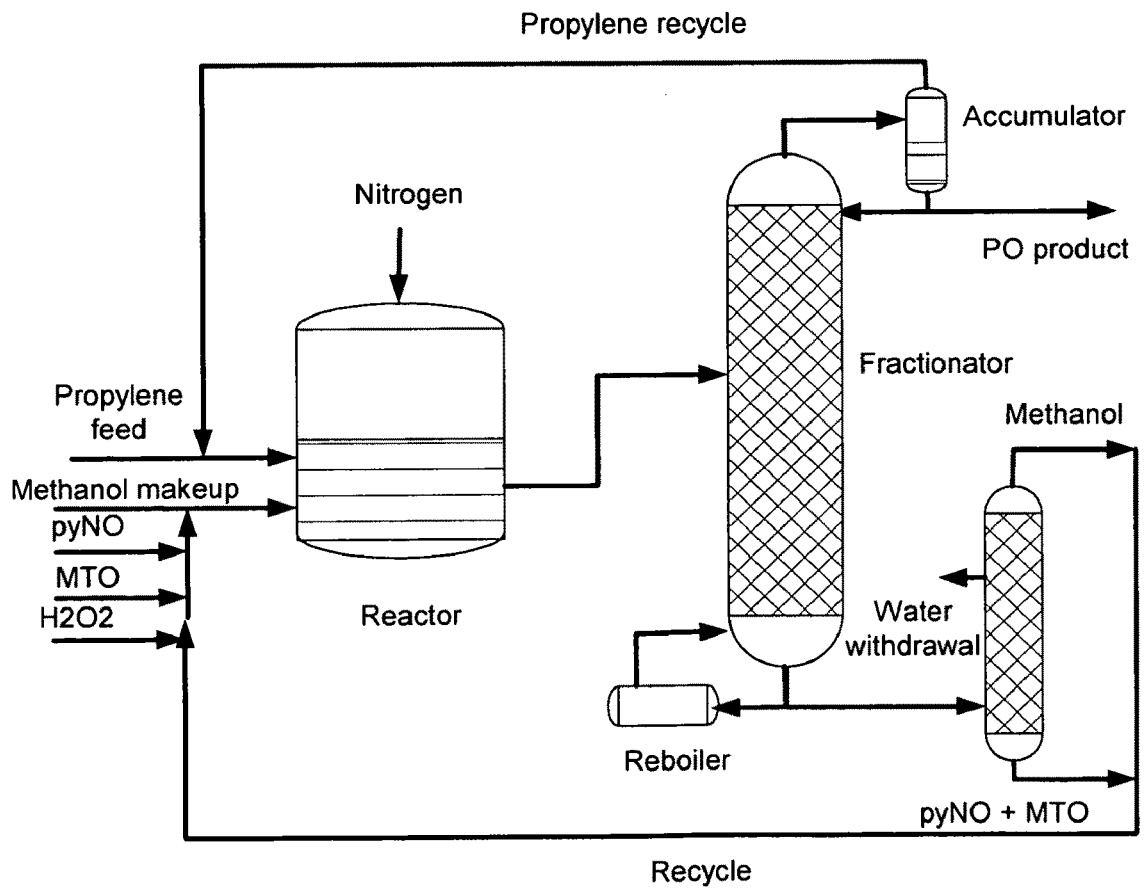
FIG. 11 is a schematic diagram of a propylene oxide production process using distillation for water separation and solvent recovery.

On the basis of the results presented herein, the most preferred reaction mixture will contain methanol, pyridine N-oxide, water, hydrogen peroxide, propylene oxide, and the MTO catalyst. Post reaction, the reactor pressure is decreased to ambient pressure causing the unreacted propylene to be released as vapor. The propylene oxide is then separated from the liquid phase by distillation around 40° C. leaving as the "bottoms product" the solvent, catalyst, and water accumulated from the water/peroxide oxidizing reagent. If methanol and catalyst are to be recycled, the main issue is separation of excess accumulated water. Reverse osmosis appears to be especially attractive to this specific system as shown in FIG. 10. Alternatively, distillation can be used for catalyst and solvent recovery as generally shown in FIG. 11.

The following are some additional considerations for these processes. First, the propylene feed position is preferentially low on the system and is directed into the liquid phase at the bottom of the tank. The feed position that returns the solvent recycle/makeup into the reactor could be higher to help absorb the propylene. However, propylene oxide would be absorbed too. Consequently, the feed position should probably be at the lower location. Second, the estimated temperature for the top/condenser would be about 30° C., the cooling water temperature to allow the condensation of PO. The bottom temperature would be in the range of 50-60° C. to promote the distillation. Lastly, the reverse osmosis ("RO") filtration is not likely to differentiate $H_2O_2$ from water. In general, small alcohol molecules are difficult to exclude from the permeate. Therefore, branched alcohols may be preferred.

Example 12

Oxidation of Ethylene Using Ethylene as a Pressurizing Gas

This example is directed to a novel selective route to form ethylene oxide from ethylene using a liquid phase process that utilizes the homogeneous catalyst MTO and aqueous hydrogen peroxide ($H_2O_2$) as the oxidant. Ethylene is transported into the liquid phase containing dissolved catalyst (MTO) and oxidant ($H_2O_2$), where it undergoes reaction to form the ethylene oxide. The ethylene oxide is easily separated by distillation given its low normal boiling point (10.8° C.) relative to other components in the system. This example demonstrates the synergy afforded by the compressibility of ethylene in the vicinity of its critical temperature (Tc=9.5° C.) and its enhanced solubility in low molecular alcohols (such as methanol) to increase its availability in the liquid phase.

In this example, methyltrioxorhenium (MTO) (71.0-76.0% Re), 50 wt % $H_2O_2$ in water and HPLC grade organic solvents (methanol, HPLC grade, greater than or equal to 99.9%), pyridine N-oxide (95%) were purchased from Aldrich and used without further purification. Ethylene was purchased from Matheson Tri-Gas Co. (Ultra high purity grade).

To determine the optimal reaction conditions, reactions in $CH_3OH/H_2O$ liquid phase were investigated using a Thar Designs Model PEA-30ML Variable Volume Phase Equilibrium Analyzer. A solution containing 50 w % $H_2O_2/H_2O$ (10.4 mmoles), pyNO (0.61 mmoles), MTO (0.084 mmoles) and $CH_3OH$ (4.1 mL) was charged into the variable volume cell. An excess of ethylene (about 0.7 g) was injected into the cell from a gas reservoir. The reactor pressure was isothermally varied (at fixed temperatures in the 20-40° C. range) by moving the piston. The existence of liquid and vapor phases was monitored visually on an external video screen.

Figure 13:
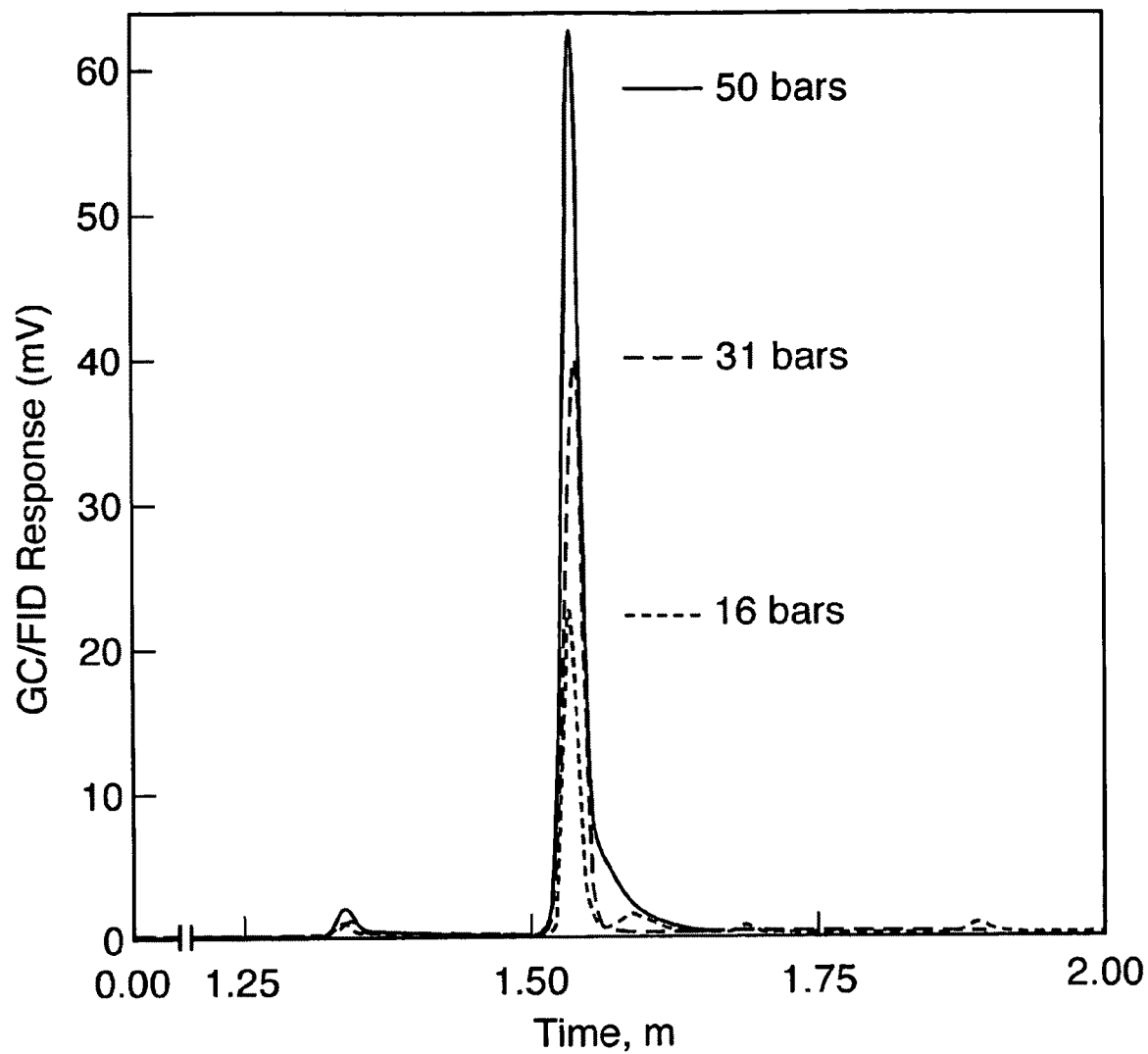
FIG. 13 is gas chromatography data showing enhanced ethylene oxide formation with pressure tuning. The feed contained 50 w % $H_2O_2/H_2O$ (10.4 mmoles), pyNO (0.61 mmoles), MTO (0.084 mmoles) and $CH_3OH$ (4.1 mL). An excess of ethylene (~0.7 g) was injected into the cell from a gas reservoir. The six-hour batch reactions were carried out at 30° C.

The isothermal batch runs, each lasting six hours, were performed in a variable volume batch reactor at different reactor pressures to understand the effect of pressure tuning on ethylene conversion and product selectivity. The products were sampled at the end of each run and analyzed by GC. As seen in FIG. 13, the ethylene oxide production increases progressively as the reactor pressure is isothermally increased from 16 to 31 to 50 bars (230 to 725 psi). This can be attributed to the increased solubility and, therefore, enhanced ethylene availability in the methanol-rich liquid phase. These experiments provided evidence of ethylene oxide formation and indicated the likelihood of an ethylene-expanded liquid effect since the yield was found to be responsive to the applied pressure in otherwise equivalent experiments.

Figure 12:
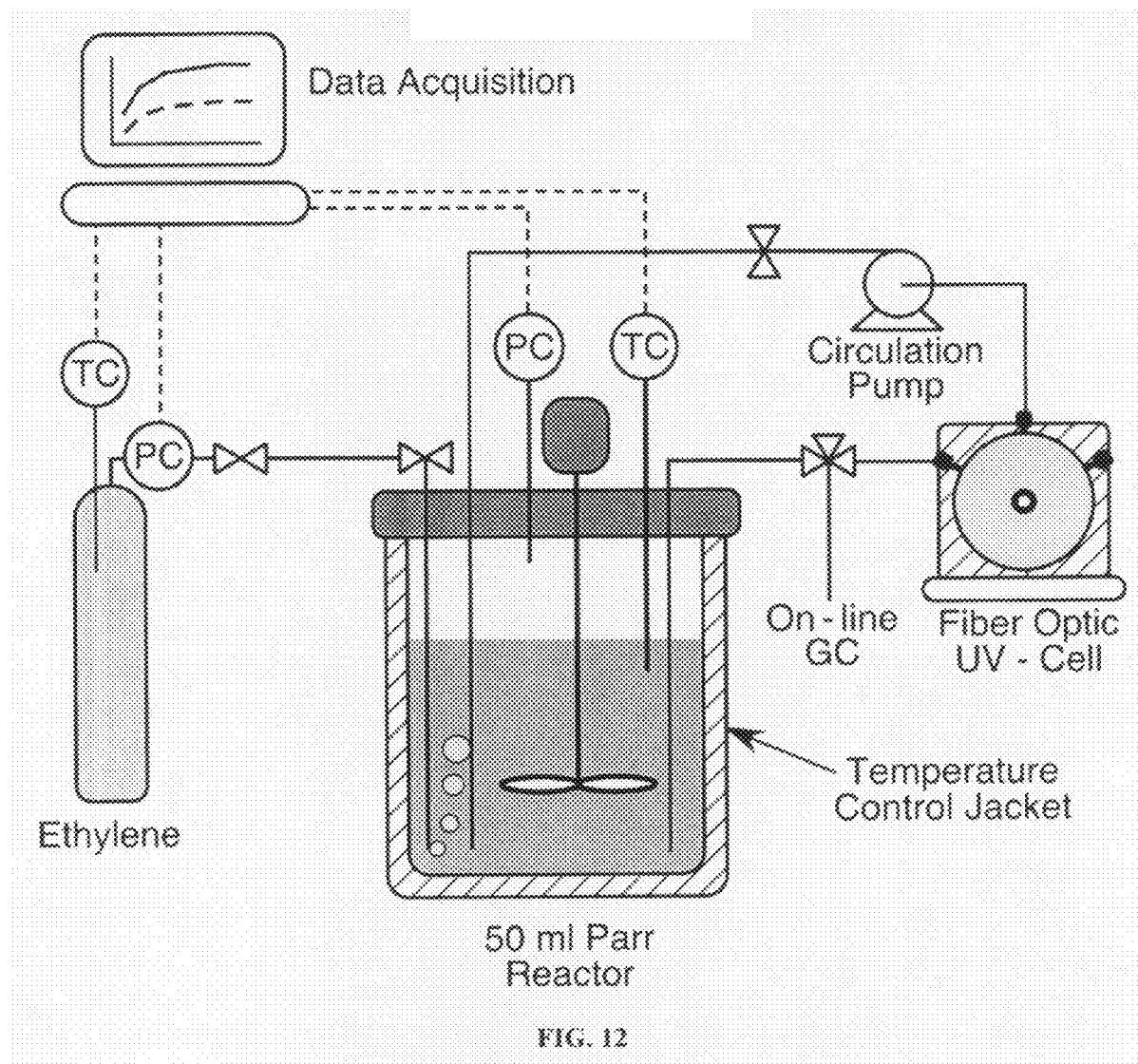
FIG. 12 is a schematic of the ethylene oxide reactor unit used in Example 12.

Next isothermal fixed volume batch runs were performed. A 50 mL Parr reactor equipped with a mechanical stirrer, pressure transducer, and thermocouple was used for more extensive studies using batch reactions. A solution containing 50 wt. % $H_2O_2/H_2O$ (8.67 mmoles), pyNO (1.82 mmoles), MTO (0.181 mmoles) and $CH_3OH$ (10 mL) was charged into the reactor and ethylene was injected from a reservoir pressurizing the reactor up to 50 bar (725 psi). The reactor pressure was maintained constant during the reaction by continually replacing the consumed ethylene from an external ethylene reservoir (FIG. 12). Isothermal, constant pressure batch reactions, each lasting 3-9 hours, were carried out over the temperature range from 20-60° C. To detect any carbon dioxide and $O_2$ generation, samples from the vapor phase were collected in a 30 mL gas reservoir and analyzed by gas chromatography at −40° C. At the end of a batch reaction, a sample is collected by cooling the reactor to −10° C. and depressurizing it slowly to remove the unreacted ethylene. The product ethylene oxide condenses in the sample trap maintained at a temperature of −40° C. with the aid of an acetone/dry ice bath. Products were analyzed with a Varian CP-3800 GC and a Varian Saturn 2100T GC/MS using a Cp-Wax58 Capillary column for liquid products and a Shimadzu CC 2014 with Shin Carbon ST packed column and an RTX-5 capillary column for gaseous products.

Figure 14:
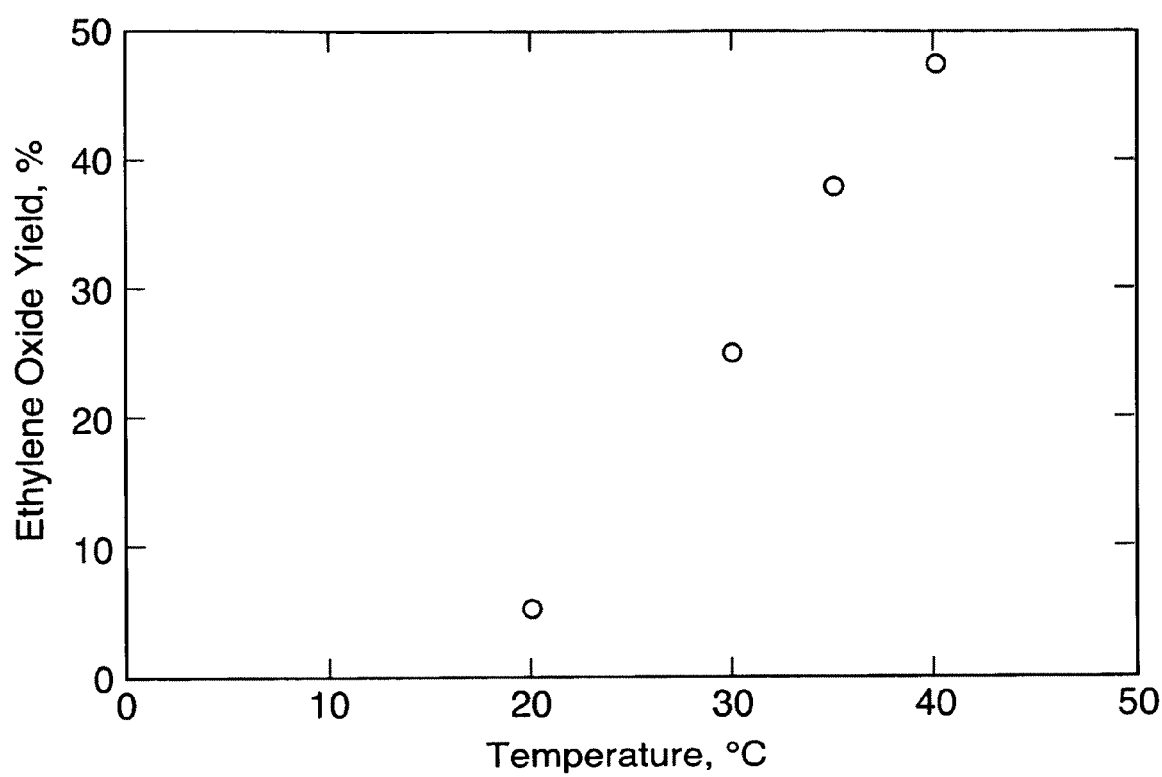
FIG. 14 shows the ethylene oxide yields at various temperatures during 6 h constant-pressure batch reactions. A solution containing 50 wt. % $H_2O_2/H_2O$ (8.67 mmoles), pyNO (1.82 mmoles), MTO (0.181 mmoles) and $CH_3OH$ (10 mL) was charged into the reactor, and the ethylene pressure was maintained at 50 bar.

Dramatic increases in productivity were found by performing fixed-volume batch runs. The ethylene oxide yield and selectivity at 40° C. are 48% and 95+% respectively. As seen in FIG. 14, the ethylene oxide yield increases steadily in the 25-40° C. range with no noticeable decomposition of either the catalyst or $H_2O_2$. Catalyst stability was inferred from the steady catalyst color and the absence of $H_2O_2$ decomposition was confirmed by the absence of measurable $O_2$ in the vapor phase.

Figure 15:
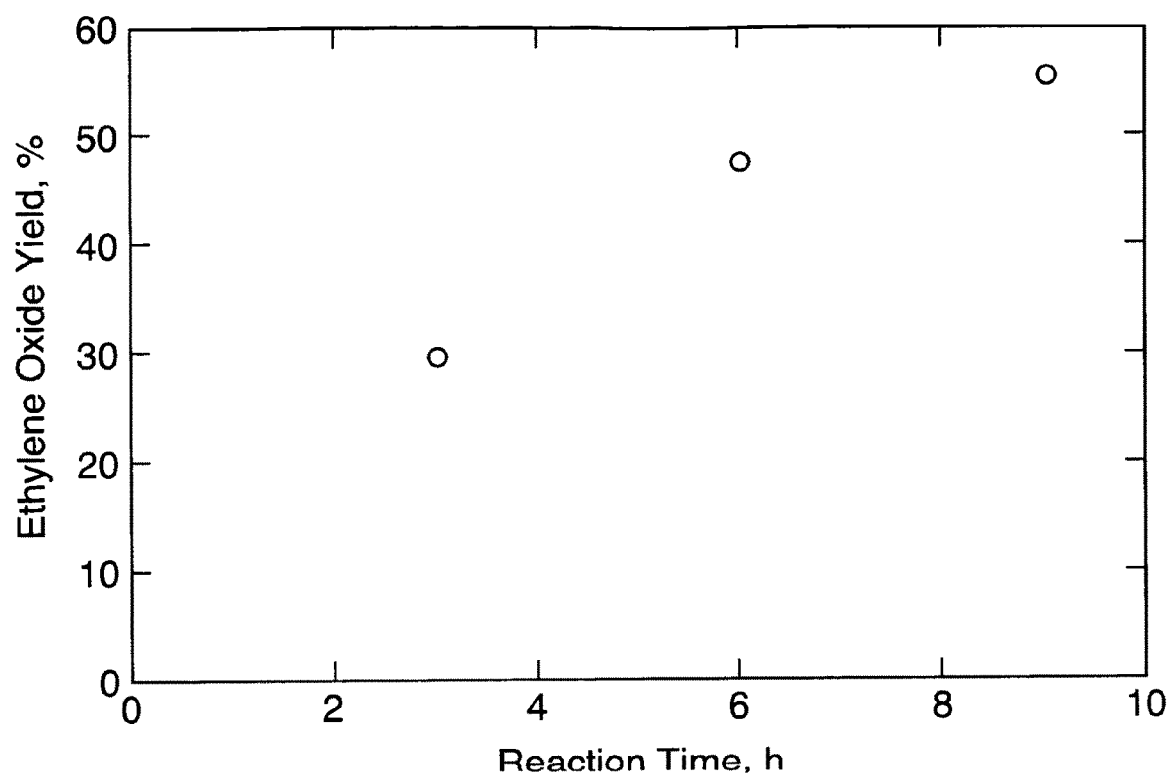
FIG. 15 shows the ethylene oxide production at 40° C. during 3-6 hour constant-pressure batch reactions. A solution containing 50 wt. % $H_2O_2/H_2O$ (8.67 mmoles), pyNO (1.82 mmoles), MTO (0.181 mmoles) and $CH_3OH$ (10 mL) was charged into the reactor, and the ethylene pressure was maintained at 50 bar.

An extended catalyst durability test lasting nine hours was performed at 40° C. and 50 bar. As shown in FIG. 15, the yellow-colored active catalyst, di-peroxo species, gradually turned pale yellow after nine hours, signifying slow decomposition under those reaction conditions. The cumulative ethylene oxide yield at the end of the nine-hour run exceeded 50% while maintaining the 95+% ethylene oxide selectivity.

The possible presence of $CO_2$ and $O_2$ in the vapor phase was determined at the end of nine-hour batch runs in the 20-40° C. range by sampling the vapor phase followed by GC analysis. GC results showed no measurable $CO_2$ or $O_2$ confirming negligible substrate combustion or oxidant demposition products at these temperatures.

The foregoing example illustrates the homogeneous liquid phase epoxidation of ethylene to ethylene oxide with MTO as catalyst and $H_2O_2$ as oxidant. The process shows promise as a viable environmentally benign and inherently safe alternative to the highly energy intensive and hazardous conventional ethylene oxide process which is associated with a large carbon foot print caused primarily by $CO_2$ emissions from combustion reactions. The high solubility of ethylene in methanol at moderate operating pressures and temperatures, elucidated by thermodynamic phase behavior modeling, was exploited to ensure that the availability of ethylene in the liquid phase is not rate limiting. The observed yield of ethylene oxide during a six hours batch reaction at 40° C. and 50 bars (725 psi) is 48% at 95+% selectivity. This observed ethylene oxide selectivity is much greater than what is attainable with current industrial technology. The absence of measurable $CO_2$ in the gas phase of the liquid epoxidation process confirms negligible burning of either the ethylene or the ethylene oxide. Furthermore, the ethylene oxide is easily separated from the aqueous phase by distillation, thereby facilitating the recycling of the catalyst. This process for ethylene epoxidation satisfies many principles of green chemistry and green engineering such as waste minimization, use of relatively benign reagents and process intensification at mild conditions. These encouraging results have provided the impetus for ongoing research to determine catalyst in-service lifetime under various operating conditions, catalyst recycling, and further enhancing the yield of ethylene oxide while maintaining high ethylene oxide selectivity.

From the foregoing it will be seen that this invention is well adapted to attain all ends and objectives herein-above set forth, together with the other advantages which are obvious and which are inherent to the invention. Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A process for epoxidizing an olefin having a critical temperature in degrees Kelvin comprising:
contacting the olefin with an oxidant in the presence of a Lewis acid oxidation catalyst and organic base in a solvent system comprising an organic water-miscible solvent to form a reaction system; and
pressurizing said reaction system to maintain a pressure between 230 and 700 psi at a reaction temperature below 60° C.

2. The process of claim 1 wherein said olefin is a light olefin selected from the group consisting of ethylene, propylene, butenes, and butadiene.

3. The process of claim 1 wherein said catalyst is an organorhenium oxide.

4. The process of claim 1 wherein said oxidant is hydrogen peroxide in an aqueous solution having about 20 to 80 wt % hydrogen peroxide.

5. The process of claim 1 wherein said oxidant is urea hydrogen peroxide.

6. The process of claim 1 wherein said olefin is ethylene and said pressurizing comprises the step of adding sufficient ethylene into said reaction system so that the pressure is between 230 and 700 psi.

7. The process of claim 1 wherein said pressurizing comprises adding a pressurizing gas which is an inert gas so that the pressure is between about 230 and 700 psi.

8. The process of claim 1 wherein said organic base is a nitrogen-containing compound selected from methylamine, diethylamine, propylamine, octylamine, trimethylamine, dimethyldodecylamine, cyclohexylamine, dicyclohexylamine, aminoethanol, diethanolamine, triethanolamine, N,N-dributylethanolamine, ethylenediamine, hexamethylenediamine, morpholine, piperidine, pyridine, 2,2'-bipyridine and 2,2',2''-tripyridine and corresponding N-oxides.

9. The process of claim 1 wherein said water miscible solvent is selected from the group consisting of acetonitrile, isopropanol, tert-butanol, methanol, and other lower alcohols.

10. The process of claim 1 wherein said solvent system consists of an organic water-miscible solvent and contains no water.

11. The process of claim 1 wherein said solvent system comprises methanol and water on a weight ratio between 3:1 to 22:1 for methanol to water.

12. The process of claim 1 wherein said reaction temperature is maintained between 0.7 to 1.3 times the critical temperature of said olefin.

13. The process of claim 1 wherein said olefin is ethylene or propylene, said oxidant is hydrogen peroxide, said solvent system comprises methanol, said base is pyridine or pyridine N-oxide, and said Lewis acid oxidation catalysis is methyltrioxorhenium, and said process forms ethylene oxide or propylene oxide at a selectivity of 95% or greater.

14. The process of claim 13 wherein said solvent system consists of an organic water-miscible solvent and contains no water.

15. The process of claim 13 wherein said solvent system consists of methanol and no water.

16. The process of claim 13 further comprising water.

17. The process of claim 1 further comprising the step of decreasing the pressure to create a vapor phase containing unreacted olefin and a liquid phase comprising the epoxidized olefin, Lewis acid oxidation catalyst, and solvent system.

18. The process of claim 17 further comprising the step of fractionating said liquid phase, thereby distilling off a first gaseous stream comprising said epoxidized olefin and forming a second liquid stream comprising said Lewis oxidation catalyst, said organic base and said solvent system comprising water and said organic water miscible solvent.

19. The process of claim 18 wherein said distilling occurs at atmospheric pressure and a temperature below about 50° C.

20. The process of claim 18 further comprising the step of separating water from said Lewis oxidation catalyst, said organic base, and said organic water miscible solvent from said second liquid stream by reverse osmosis.

21. The process of claim 20 further comprising the step of recycling said oxidation catalyst to said contacting step.

22. The process of claim 21 wherein said recycling step also comprises the step of recycling said organic base and said organic water miscible solvent to said contacting step.

23. The process of claim 18 further comprising the step of separating said oxidation catalyst, said organic base, and said organic water miscible solvent from said second stream by distillation.

24. The process of claim 23 further comprising the step of recycling said separated oxidation catalyst to said contacting step.

25. An epoxidation reaction system comprising:
an olefin to be epoxidized, said olefin having a critical temperature in degrees Kelvin; an oxidant; a Lewis acid oxidation catalyst; and an organic base in a solvent system comprising an organic water-miscible solvent; and
wherein said reaction system is maintained at a pressure between about 100 to 1000 psi and wherein said system has a reaction temperature less than 60° C., and wherein the selectivity is greater than 95%.

26. The reaction system of claim 25 wherein said olefin is ethylene, propylene, butenes, or butadienes.

27. The reaction system of claim 25 wherein said pressure is maintained by adding an inert pressurizing gas to said system.

28. The reaction system of claim 25 wherein said organic base is selected from methylamine, diethylamine, propylamine, octylamine, trimethylamine, dimethyldodecylamine, cyclohexylamine, dicyclohexylamine, aminoethanol, diethanolamine, triethanolamine, N,N-dributylethanolamine, ethylenediamine, hexamethylenediamine, morpholine, piperidine, pyridine, 2,2'-bipyridine, and 2,2',2"-tripyridine, and corresponding N-oxides.

29. The reaction system of claim 25 wherein said water miscible solvent is selected from the group consisting of isopropanol, acetonitrile, tert-butanol, and methanol.

30. The reaction system of claim 25 wherein said solvent system consists of an organic water-miscible solvent and contains no water.

31. The reaction system of claim 25 wherein said solvent system comprises methanol and water having a weight ratio from 3:1 to 22:1 for methanol to water.

32. The reaction system of claim 25 wherein said system is maintained at a reaction temperature between 0.7 to 1.3 times the critical temperature of the olefin.

33. The reaction system of claim 25 wherein said olefin is ethylene or propylene, said oxidant is hydrogen peroxide, said solvent system comprises methanol, said base is pyridine or pyridine N-oxide, said Lewis acid oxidation catalyst is methyltrioxorhenium, and said pressure is between about 230 to 700 psi.

34. The reaction system of claim 33 wherein said solvent system consists of an organic water-miscible solvent and contains no water.

35. A process for epoxidizing an olefin comprising:
selecting an epoxidation reaction system comprising an olefin to be epoxidized, said olefin having a critical temperature in degrees Kelvin ($T_c$); an oxidant; a Lewis acid oxidation catalyst; and an organic base; and a solvent system comprising an organic water-miscible solvent; and
reacting said reaction system at an epoxidizing reaction temperature which is 0.7 to 1.3 times the $T_c$ and at a pressure maintained between 230 and 1000 psi.

36. The process of claim 35 wherein said olefin is ethylene.

37. The process of claim 36 wherein said oxidant is hydrogen peroxide.

38. The process of claim 37 wherein said oxidation catalyst is methyltrioxorhenium and said base is pyridine N-oxide.

39. The process of claim 35 where said olefin is epoxidized at a selectivity of 95% or greater.

40. A process for epoxidizing a light olefin comprising:
providing an epoxidation reaction system comprising said light olefin to be epoxidized, said olefin having a critical temperature in degrees Kelvin ($T_c$); an oxidant; a Lewis acid oxidation catalyst; and an organic base; and a solvent system comprising an organic water-miscible solvent; and
reacting said reaction system at an epoxidizing reaction temperature which is 0.7 to 1.3 times the $T_c$ and at a pressure maintained between 100 and 1000 psi to provide an epoxidation yield greater than 90%.

41. The process of claim 40 wherein said pressure is between 230 and 700 psi.

42. The process of claim 40 wherein said olefin is selected from the group consisting of ethylene, propylene, butenes, and butadiene.

43. The process of claim 42 where said olefin is epoxidized at a selectivity of 95% or greater.

44. The process of claim 42 wherein said oxidant is hydrogen peroxide.

45. The process of claim 42 wherein said reaction system includes the step of pressurizing said system with an inert gas having a pressure between 100 and 1000 psi.

46. The process of claim 42 wherein said react occurs for three hours or less.

47. A process for epoxidizing an olefin comprising:
selecting an epoxidation reaction system comprising an olefin to be epoxidized, said olefin having a critical temperature in degrees Kelvin ($T_c$), said olefin selected from the group consisting of ethylene, propylene, butenes, and butadiene; an oxidant; a Lewis acid oxidation catalyst; and an organic base; and a solvent system comprising an organic water-miscible solvent; and
reacting said reaction system at an epoxidizing reaction temperature which is 0.7 to 1.3 times the $T_c$ and at a pressure maintained between 100 and 1000 psi.

48. The process of claim 47 wherein said pressure is between 230 and 700 psi.

49. The process of claim 47 wherein said olefin is epoxidized at a selectivity of 95% or greater.

50. The process of claim 47 wherein said olefin is epoxidized at a yield of 90% or greater.

51. The process of claim 47 wherein said oxidant is hydrogen peroxide.

52. The process of claim 47 wherein said reaction system includes an inert gas having a pressure between 100 and 1000 psi.

53. The process of claim 47 wherein said reacting occurs for three hours or less.

54. The process of claim 47 wherein said reacting provides for an epoxidation yield greater than 90%.

55. The process of claim 47 wherein said reacting provides for an epoxidation yield greater than 95%.

56. The process of claim 47 wherein said reacting provides for an epoxidation selectivity greater than 95%.

57. The process of claim 47 wherein said reaction undergoes mechanical stirring.

58. The process of claim 1 wherein said reaction undergoes mechanical stirring.

59. The process of claim 25 wherein said reaction undergoes mechanical stirring.

60. The process of claim 35 wherein said reaction undergoes mechanical stirring.

61. The process of claim 40 wherein said reaction undergoes mechanical stirring.

* * * * *